United States Patent [19]

Ehrenfreund et al.

[11] Patent Number: 4,888,348

[45] Date of Patent: Dec. 19, 1989

[54] SUBSTITUTED THIOUREAS, ISOTHIOUREAS AND CARBODIIMIDES

[75] Inventors: Josef Ehrenfreund, Allschwil, Switzerland; Manfred Böger, Weil am Rhein, Fed. Rep. of Germany; Odd Kristiansen, Möhlin, Switzerland; Jozef Drabek, Oberwil, Switzerland; Haukur Kristinsson, Basel, Switzerland

[73] Assignee: Ciba-Geigy Corporation, Ardsley, N.Y.

[21] Appl. No.: 91,157

[22] Filed: Aug. 28, 1987

[30] Foreign Application Priority Data

Sep. 4, 1986 [CH] Switzerland .................. 3561/86

[51] Int. Cl.$^4$ .............. C07D 777/34; C07D 277/68; A01N 47/30; A01N 43/78
[52] U.S. Cl. ............................. 514/367; 514/369; 548/165; 548/169; 548/171; 548/186; 548/187; 548/189; 548/129; 548/136; 548/144; 548/221; 548/262; 548/265; 548/337; 549/65; 549/66
[58] Field of Search ............ 548/171, 187, 189, 169, 548/165, 186; 514/367, 369

[56] References Cited

U.S. PATENT DOCUMENTS

| | | | |
|---|---|---|---|
| 3,231,610 | 10/1962 | Kühle et al. ............ | 260/551 |
| 3,940,392 | 2/1976 | Johnston ............ | 260/250 |
| 3,947,437 | 3/1976 | Johnston ............ | 260/250 |
| 4,518,682 | 5/1985 | Kobayashi ............ | 430/543 |
| 4,611,060 | 9/1986 | Haberkorn ............ | 548/171 |

FOREIGN PATENT DOCUMENTS

| | | | |
|---|---|---|---|
| 105735 | 4/1984 | European Pat. Off. . | |
| 201030 | 11/1986 | European Pat. Off. ............ | 548/171 |
| 2501648 | 7/1975 | Fed. Rep. of Germany . | |
| 2553270 | 6/1977 | Fed. Rep. of Germany . | |
| 5879979 | 5/1983 | Japan . | |
| 649990 | 6/1985 | Switzerland . | |
| 2060626 | 5/1981 | United Kingdom . | |

*Primary Examiner*—Robert Gerstl
*Attorney, Agent, or Firm*—Edward McC. Roberts

[57] ABSTRACT

The invention relates to novel substituted phenylthioureas, phenylisothioureas and phenylcarbodiimides of formula I

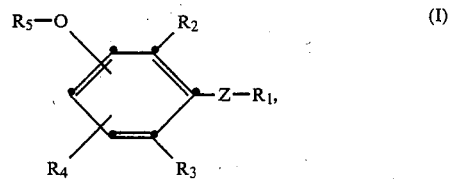

(I)

wherein Z is

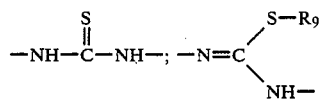

or —N=C=N—;

$R_1$ is $C_1$-$C_{12}$alkyl, $C_3$-$C_{10}$alkenyl, $C_3$-$C_{10}$alkynyl, $C_3$-$C_8$cycloalkyl, $C_1$-$C_3$alkyl substituted by 1 or 2 $C_3$-$C_6$cycloalkyl radicals, or is alkoxyalkyl containing a total of 3 to 10 carbon atoms, halogen-substituted $C_1$-$C_{12}$alkyl, polycyclic $C_7$-$C_{10}$cycloalkyl, or phenyl($C_1$-$C_5$)alkyl which may be substituted in the phenyl moiety by 1 or 2 identical or different members selected from the group consisting of halogen, methoxy, ethoxy and $C_1$-$C_5$alkyl, $R_2$ is hydrogen or $C_1$-$C_5$alkyl, $R_3$ is $C_1$-$C_5$alkyl or $C_3$-$C_6$cycloalkyl, $R_4$ is hydrogen or $C_1$-$C_4$alkyl, $R_5$ is a 5-membered heterocyclic radical containing 1 to 4 hetero atoms selected from the group consisting of N, O and S, which radical may be substituted at the carbon or nitrogen atoms by 1 to 3 of the substituents $R_6$, $R_7$ and $R_8$, or is a 5-membered heterocyclic radical which may be fused with benzene nuclei and which contains 1 or 2 hetero atoms selected from the group consisting of N, O and S and can be substituted at the carbon or nitrogen atoms by 1 to 3 of the substituents $R_6$, $R_7$ and $R_8$, $R_6$ and $R_7$ are each independently of the other hydrogen, halogen, $C_1$-$C_4$alkyl, halogen-substituted $C_1$-$C_4$alkyl, $C_1$-$C_4$alkoxy; halogen-substituted $C_1$-$C_4$alkoxy, phenyl, or $C_1$-$C_4$alkylthio, $R_8$ is hydrogen or $C_1$-$C_4$alkyl, and $R_9$ is $C_1$-$C_5$alkyl, $C_2$-$C_5$alkenyl, $C_3$-$C_4$alkynyl, alkoxyalkyl containing a total of 10 carbon atoms, or alkylthioalkyl containing a total of 10 carbon atoms and to the salts thereof with acids and bases. The invention further relates to the preparation of these compounds and to the use thereof in pest control, and to novel intermediates.

22 Claims, No Drawings

SUBSTITUTED THIOUREAS, ISOTHIOUREAS AND CARBODIIMIDES

The present invention relates to novel thioureas, isothioureas and carbodiimides which are substituted by 5-membered heterocyclic radicals, to their preparation and to the use thereof in pest control.

Insecticidal and acaricidal N-(phenoxyphenyl)-N'-alkylthioureas and N-(phenoxyphenyl)-N'-alkylisothioureas are disclosed in UK patent application No. 2 060 626 and in European patent specification No. 0 025 010. Corresponding N-pyridyloxyphenyl-N'-tert-butylthioureas and N-pyridyloxyphenyl-N'-tert-butylisothioureas are disclosed in Japanese patent publication No. 58-79979. Further, insecticidal and acaricidal N-pyridyloxyphenyl-N'-alkylcarbodiimides are disclosed in European patent application No. 0 174 649. The thioureas, isothioureas and carbodiimides of formula I below of this invention differ structurally from these prior art compounds essentially in that that they contain a N-phenyl group which is substituted by a 5-membered heterocyclic ring which is bound through an oxygen atom. The aforementioned types of compound known from the prior art are not entirely satisfactory with respect to duration of action, potency and breadth of activity. Surprisingly, it has now been found that the compounds of formula I of this invention are highly suitable for use as pesticides.

The compounds of the present invention have the formula I

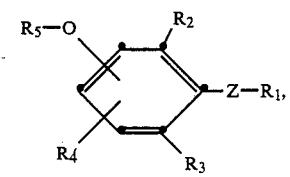

wherein
Z is

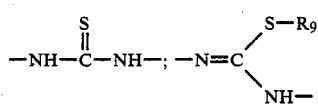

or —N=C=N—;

$R_1$ is $C_1$–$C_{12}$alkyl, $C_3$–$C_{10}$alkenyl, $C_3$–$C_{10}$alkynyl, $C_3$–$C_8$cycloalkyl, $C_1$–$C_3$alkyl, substituted by 1 or 2 $C_3$–$C_6$cycloalkyl radicals, or is alkoxyalkyl containing a total of 3 to 10 carbon atoms, halogen-substituted $C_1$–$C_{12}$alkyl, polycyclic $C_7$–$C_{10}$cycloalkyl, or phenyl($C_1$–$C_5$)alkyl which may be substituted in the phenyl moiety by 1 or 2 identical or different members selected from the group consisting of halogen, methoxy, ethoxy and $C_1$–$C_5$alkyl, $R_2$ is hydrogen or $C_1$–$C_5$alkyl, $R_3$ is $C_1$–$C_5$alkyl or $C_3$–$C_6$cycloalkyl, $R_4$ is hydrogen or $C_1$–$C_4$alkyl, $R_5$ is a 5-membered heterocyclic radical containing 1 to 4 hetero atoms selected from the group consisting of N, O and S, which radical may be substituted at the carbon or nitrogen atoms by 1 to 3 of the substituents $R_6$, $R_7$ and $R_8$, or is a 5-membered heterocyclic radical which may be fused with benzene nuclei and which contains 1 or 2 hetero atoms selected from the group consisting of N, O and S and can be substituted at the carbon or nitrogen atoms by 1 or 3 of the substituents $R_6$, $R_7$ and $R_8$, $R_6$ und $R_7$ are each independently of the other hydrogen, halogen, $C_1$–$C_4$alkyl, halogen-substituted $C_1$–$C_4$alkyl, $C_1$–$C_4$alkoxy, halogen-substituted $C_1$–$C_4$alkoxy, phenyl, or $C_1$–$C_4$alkylthio, $R_8$ is hydrogen or $C_1$–$C_4$alkyl, and $R_9$ is $C_1$–$C_5$alkyl, $C_2$–$C_5$alkenyl, $C_3$–$C_4$alkynyl, alkoxyalkyl containing a total of 10 carbon atoms, or alkylthioalkyl containing a total of 10 carbon atoms.

The invention also relates to salts of compounds of formula I with suitable acids and bases.

In this specification, individual representatives of the hetero-cyclic 5-membered radicals present in the compounds of this invention are referred to in abbreviated form as follows:

$Q_1$ is thiazolyl, $Q_2$ is 1,2,4-triazolyl, $Q_3$ is 1,3,4-thiadiazolyl, $Q_4$ is 1,2,4-thiadiazolyl, $Q_5$ is 1,3,4-oxadiazolyl, $Q_6$ is thienyl, $Q_7$ is benzoxazolyl, $Q_8$ is benzthiazolyl, $Q_9$ is imidazolyl, $Q_{10}$ is furanyl, $Q_{11}$ is pyrrolyl, $Q_{12}$ is pyrazolyl, $Q_{13}$ is oxazolyl, $Q_{14}$ is benzofuranyl, $Q_{15}$ is indolyl, $Q_{16}$ is benzimidazolyl and $Q_{17}$ is tetrazolyl.

Preferred compounds of formula I are those in which the substituents $R_1$ to $R_4$, Z and $R_6$ to $R_9$ are as previously defined and in which the substituent $R_5$ denotes the following heterocyclic radicals:

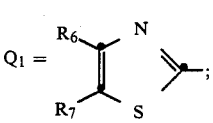

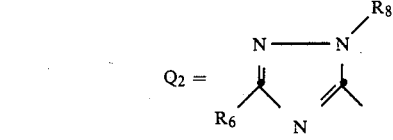

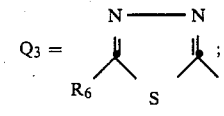

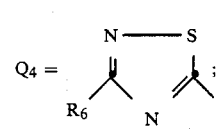

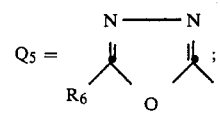

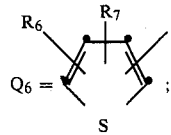

-continued

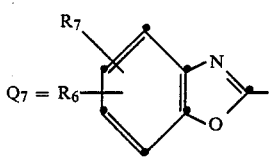

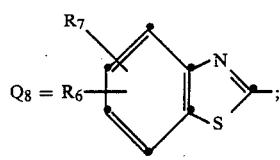

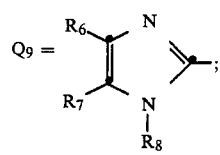

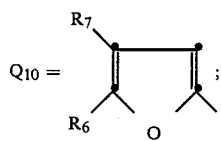

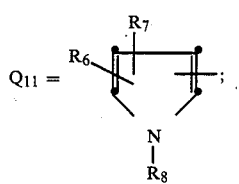

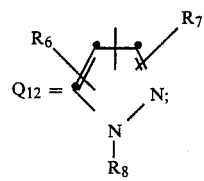

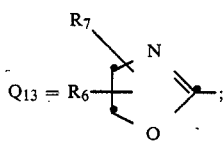

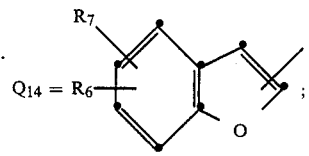

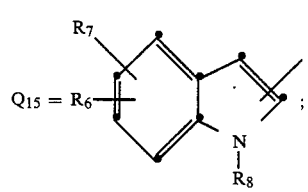

-continued

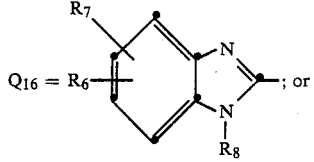

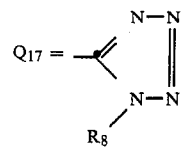

Compounds of formula I meriting particular interest are those wherein the group $R_5O$ is in para-position to the group Z and Z is

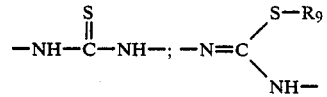

or $-N=C=N-$;

$R_1$ is $C_3-C_7$alkyl, cyclopentyl, cyclohexyl, (dicyclopropyl)methyl, or alkoxyalkyl of 4 carbon atoms, $R_2$ $R_3$ are each independently of the other $C_1-C_3$alkyl, $R_3$ and $R_4$ are hydrogen, $R_5$ is a heterocyclic radical selected from the group consisting of

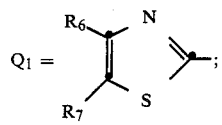

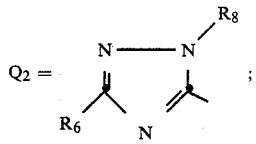

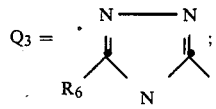

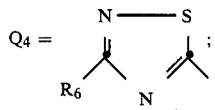

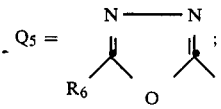

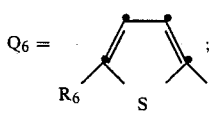

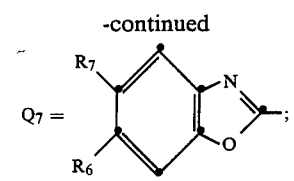

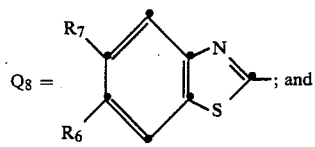

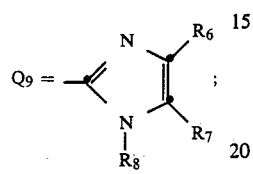

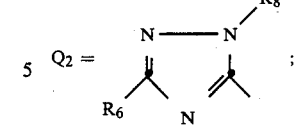

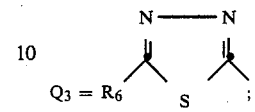

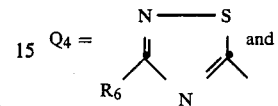

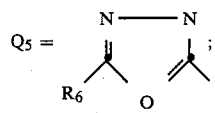

$R_6$ is hydrogen, chlorine, bromine, $C_1$-$C_4$alkyl, $C_1$-$C_3$perfluoralkyl, or phenyl;
$R_7$ is hydrogen, chlorine, bromine, or $C_1$-$C_4$alkyl,
$R_8$ is hydrogen, or $C_1$-$C_3$alkyl, and
$R_9$ is methyl or ethyl, and the salts thereof with hydrohalic acids.

Particularly preferred compounds of formula I are those wherein the group $R_5O$ is in para-position to the group Z and
Z is

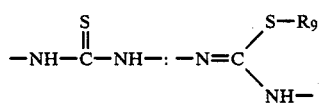

or —N=C=N—;
$R_1$ is tert-butyl, tert-pentyl, $C_5$-$C_6$cycloalkyl or 3-methoxypropyl;
$R_2$ and $R_3$ are each independently of the other $C_1$-$C_3$alkyl,
$R_4$ is hydrogen,
$R_5$ is a heterocyclic radical selected from the group consisting of

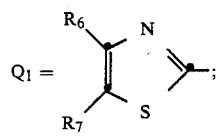

$R_6$ is $C_1$-$C_4$alkyl, chlorine, bromine, or $C_1$-$C_3$perfluoroalkyl,
$R_7$ is hydrogen, chlorine, bromine or $C_1$-$C_4$alkyl,
$R_8$ is $C_1$-$C_3$alkyl,
$R_9$ is methyl or ethyl, and the salts thereof with hydrohalic acids.

Novel substituted thioureas falling under the general formula I (Z=—NH—CS—NH—) have the formula Ia

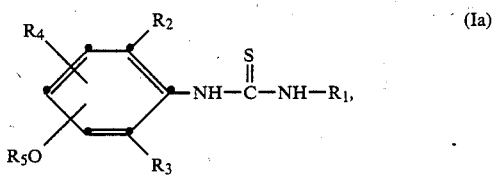

and the novel substituted carbodiimides (Z=—N=C=N—) have the formula Ic

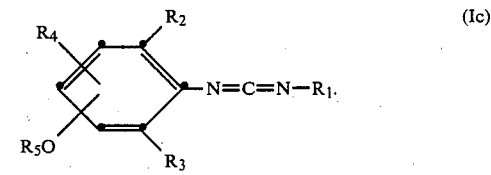

The novel substituted isothioureas of this invention can be obtained in their tautomeric forms of formulae Ib and Ib″

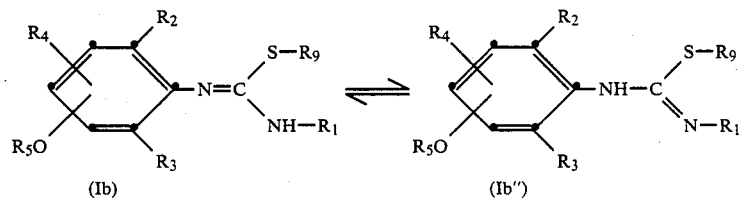

The invention encompasses both tautomeric forms as such as well as mixtures thereof. In the foregoing formulae $R_1$ to $R_5$ and $R_9$ are as defined above.

The compounds of formula I can be obtained in the form of addition salts of inorganic or organic acids and can also be used in the practice of this invention in the form of their salts. Accordingly, compounds of formula I will be understood as meaning within the scope of this invention the free compounds of formula I as well as the acid addition salts thereof.

The compound of formula I can be converted into their acid addition salts by methods which are known per se. Examples of acids suitable for forming acid addition salts are: hydrochloric acid, hydrobromic acid, hydroidic acid, nitric acid, phosphoric acid, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid, phenylsulfonic acid and salicylic acid.

Within the scope of this invention, alkyl will be understood as meaning straight chain and branched alkyl radicals and, depending on the indicated number of carbon atoms, e.g. the following groups: methyl, ethyl, propyl, butyl, pentyl and the like, as well as the isomers thereof, e.g. isopropyl, isobutyl, tert-butyl, isoamyl, tert-pentyl and the like. Halogen will be understood as meaning fluorine, chlorine, bromine and iodine, with fluorine and chlorine being preferred.

The term "haloalkyl" will be understood as meaning within the scope of this invention straight chain and branched alkyl radicals such as methyl and ethyl, n-propyl, isopropyl and the isomers of butyl, which radicals are substituted by up to 9 different or identical halogen atoms. These radicals may be perhalogenated alkyl radicals or also those in which only some of the hydrogen atoms are substituted by halogen. Examples of haloalkyl radicals are the perfluoroalkyl radicals trifluoromethyl, pentafluoroethyl or heptafluoro-n-propyl.

The compounds of formula I are novel and can be prepared by methods which are known per se, e.g.

(a) by addition of an amine of formula VI to an isothiocyanate of formula II

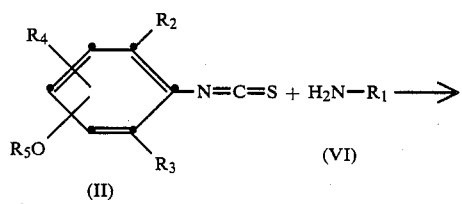
(II) (VI)

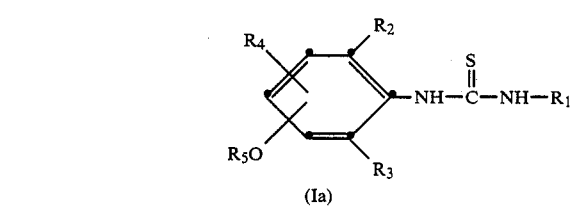
(Ia)

to give a thiourea of formula Ia, or (b) by alkylating a thiourea of formula Ia with a compound of formula VII

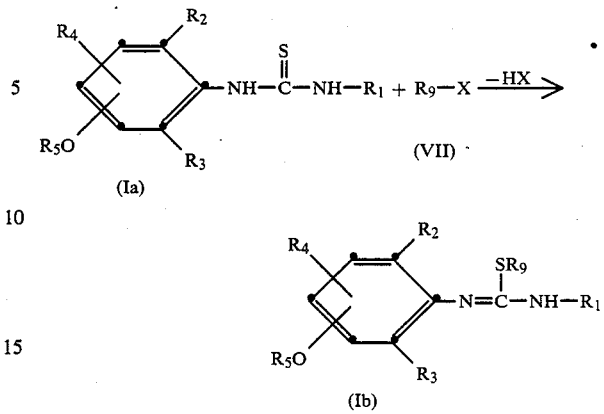

wherein X is a group which can be removed under the reaction conditions, to form an isothiourea of formula Ib. X is preferably a halogen atom, e.g. a chlorine, bromine or iodine atom, a sulfate or a halogenated or alkylated sulfate, e.g. a mesylate, brosylate, tosylate or a dialkyl sulfate, e.g. dimethyl sulfate (q.v. also J. B. Hendrickson et al., "Organic Chemistry", McGraw-Hill Book Co., 1970, pp. 378–382). An isothiourea of formula Ib can also be obtained by treating the isothiouronium salt mainly formed under the reaction conditions with a base (e.g. an alkali metal hydroxide or alkali metal carbonate); or (c) by removing hydrogen sulfide from a thiorea of formula Ia with a suitable reagent, e.g. 2-chloro-1-methylpyridinium iodide, in the presence of a base, in accordance with the reaction scheme:

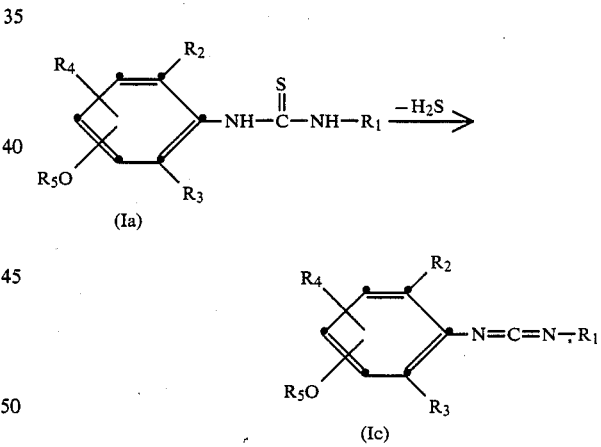

to form a carbodiimide of formula Ic. The elimination reaction to give the carbodiimide of formula Ic can be carried out in accordance with procedures known from the literature, e.g. with the aid of $H_gO$, specific pyridinium salts, chloroacetates, cyanuric chloride, p-toluenesulfochloride or specific phosphate derivatives [T. Shibanuma, Chemistry Letters (1977), pp. 575–6; S. Kim, Tetrahedron Letters (1985), pp. 1661–1664; W. Weith, B.6 (1873) 1398; G. Amiard, Bull. Soc. chim. 1956, 1360].

The above processes (a), (b) and (c) are conveniently carried out in the temperature range from 0° to 150° C., e.g. from 20° to 80° C., under normal or slightly elevated pressure, and preferably in the presence of a solvent or diluent which is inert to the reactants. Examples of suitable solvents or diluents are: ethers and ethereal compounds such as diethyl ether, diisopropyl ether, dioxane and tetrahydrofuran; aromatic hydrocarbons such as benzene, toluene and xylenes; ketones such as acetone, methyl ethyl ketone and cyclohexanone; dimethylformamide and acetonitrile. Alcohols such as ethanol, methanol, propanol or isopropanol are suitable only for processes (a) and (b).

The phenylisothiocyanates of formla II are novel and likewise constitute an object of the invention. They can be prepared in a manner known per se, e.g. by reacting an aniline of formula III with thiophosgene in the presence of a base such as calcium carbonate (q.v. S. Patai ed. "The Chemistry of Cyanates and their Thio Derivatives", Part. 2, p. 1032 et seq., Wiley 1977):

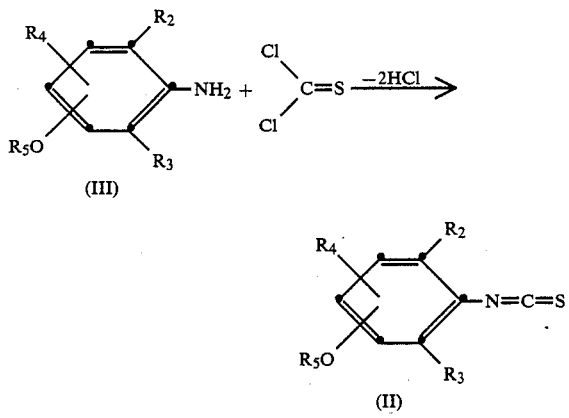

The anilines of formula III are also novel compounds. They can be obtained e.g. by condensing suitably substituted aminophenols IV, in the presence of a base, with compounds of formual V (q.v. J. Am. Soc. Perkin I, 1981, 2335; Bull. Sc. Chim. Fr. 1962, 1735; DE-OS 2 252 070; A. Weissberger et al., "The Chemistry of Heterocyclic Compounds", Vol. 34, I, 565 et seq.):

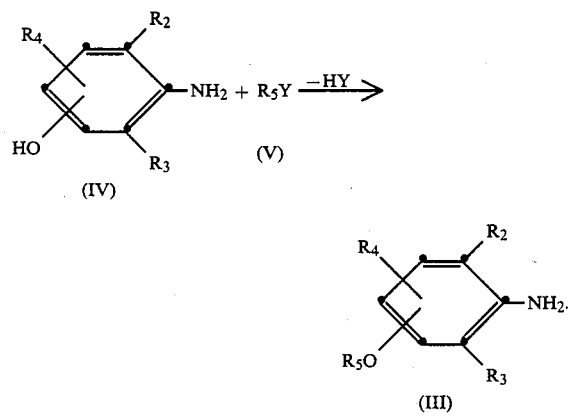

Y is formula V is a group which can be removed under the reaction conditions, e.g. a halogen atom (preferably a chlorine, bromine or iodine atom) or $C_1$–$C_4$alkylsulfonyl (e.g. methylsulfonyl). The anilines of formula III are thus also useful starting compounds and constitute an object of the invention.

In addition to their insecticidal properties, the thioureas of formula Ia are—as mentioned—also useful starting materials for the preparation of the isothioureas of formula Ib and of the carbodiimides of formula Ic. The use of the thioureas of formula Ia as intermediates for the synthesis of compounds for formula Ib and Ic thus constitutes a further object of the invention.

Surprisingly, it has been found that the compounds of formula I have excellent pesticidal properties while being well tolerated by plants and having low toxicity to warm-blooded animals. They are especially suitable for controlling pests that attack plants and animals.

The compounds of formula I (viz. Ia, Ib and Ic) are particularly effective against plant-destructive acarids (spider mites e.g. of the families Tetranychidae, Tarsonemidae, Eriophydae, Tyroglyphidae and Glycyphagidae) and also against ectoparasitic acarids (mites and ticks e.g. of the families Ixodidae, Argasidae, Sarcoptidae and Dermanissidae) that attack productive livestock. A number of the compounds of this invention have good acaricidal-ovicidal activity and leaf penetration properties. The compounds of formula I are particularly suitable for controlling the following species of mites which attack crops of fruit and vegetables: Tetranychus urticae, Tetranychus cinnabarinus, Panonychus ulmi, Broybia rubrioculus, Panonychus citri, Eriophyes piri, Eriophyes ribis, Eriophyes vitis, Tarsonemus pallidus, Phyllocoptes vitis and Phyllocoptruta oleivora.

Furthermore, is has been found that the compounds of formula I also have insecticidal properties and are thus particularly suitable for controlling plant-destructive and ectoparasitic insects e.g. of the orders Lepidoptera, Coleoptera, Heteroptera, Diptera, Orthoptera and Homoptera.

In addition to their very good action against flies, e.g. Musca domestica, and mosquito larvae, the compounds of formula I are suitable for controlling plant-destructive feeding insects in ornamental and crops of useful plants, especially in cotton (e.g. against Spodoptera Litteralis and Heliothis virescens) and in vegetables (e.g. against Leptinotarsa decemlineata and Plutella xylostella).

The compounds of formula I are also suitable for controlling ectoparasites such as Lucilia sericata, in domestic animals and productive livestock, e.g. by treating animals, cowsheds, barns, stables, and pastures.

The good pesticidal activity of the compounds of formula I of the invention corresponds to a mortality of at least 50–60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral filers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt or lignosulfonic acid, of dodecylsulfate, or of a mixture of fatty alcohol sulfates obtained from natural fatty acids. These compounds also comprise the salts of sulfates and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp. Ridgewood, New Jersey, 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or combination thereof with other insecticides or acaricides, 1 to 99% of a solid or liquid adjuvant, and 0 to 25%, preferably 0.1 to 20%, of a surfactant.

Whereas commercial products are preferably formulated as concentrates, the end user will normally employ dilute formulations of substantially lower concentration, e.g. from 0.1 to 1000 ppm.

In the following experimental Examples the indicated melting points in °C. are uncorrected.

EXAMPLE 1

Preparation of 2,6-dimethyl-4-(4-bromothiazol-2-yloxy)aniline 10.0 g of 2,4-dibromothiazole, 5,65 g of 3,5-dimethyl-4-aminophenol, 7,4 g of potassium carbonate and 50 ml of dry dimethylsulfoxide are mixed and the mixture is kept for 23 hours at 90° C. The reaction mixture is poured into 300 ml of ice-water and extracted with ether. The ethereal phases are washed with a 10% solution of sodium hydroxide and with water, dried over sodium sulfate, and purified by chromatography through a column of siliva gel with a 1:1 mixture of hexane/ethyl acetate.

The title compound of formula

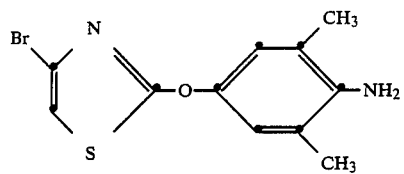

is isolated in the form of crystals with a melting point of 115°–117° C. (compound 1.01).

The following anilines of formula III' are prepared in accordance with the above procedure:

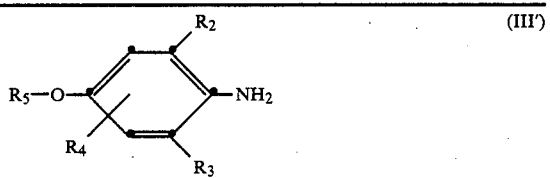

| Comp. | R$_2$ | R$_3$ | R$_4$ | R$_5$ | R$_6$ | R$_7$ | R$_8$ | Physical data (°C.) |
|---|---|---|---|---|---|---|---|---|
| 1.01 | CH$_3$ | CH$_3$ | — | Q$_1$ | Br | H | — | m.p. = 115–7.5° |
| 1.02 | C$_2$H$_5$ | C$_2$H$_5$ | — | Q$_1$ | CF$_3$ | Br | — | m.p. = 72–4° |
| 1.03 | CH$_3$ | CH$_3$ | — | Q$_1$ | Br | Cl | — | m.p. = 82–6° |
| 1.04 | CH$_3$ | CH$_3$ | — | Q$_1$ | Br | Br | — | m.p. = 90–2° |
| 1.05 | CH$_3$ | CH$_3$ | — | Q$_1$ | Cl | Br | — | m.p. = 86–8° |
| 1.06 | CH$_3$ | CH$_3$ | — | Q$_1$ | Cl | Cl | — | m.p. = 74.5–6° |
| 1.07 | CH$_3$ | CH$_3$ | — | Q$_1$ | Cl | H | — | m.p. = 120° |
| 1.08 | CH$_3$ | CH$_3$ | — | Q$_1$ | CF$_3$ | H | — | m.p. = 109–10° |
| 1.09 | CH$_3$ | CH$_3$ | — | Q$_1$ | CF$_3$ | Br | — | m.p. = 86–87° |
| 1.10 | C$_2$H$_5$ | C$_2$H$_5$ | — | Q$_1$ | Cl | Cl | — | m.p. = 58–60° |
| 1.11 | C$_2$H$_5$ | C$_2$H$_5$ | — | Q$_1$ | Cl | Br | — | m.p. = 55–56° |
| 1.12 | CH$_3$ | CH$_3$ | — | Q$_2$ | CF$_3$ | — | CH$_3$ | m.p. = 155–156° |
| 1.13 | CH$_3$ | CH$_3$ | — | Q$_2$ | CF$_3$ | — | C$_3$H$_7$(i) | m.p. = 153–155° |
| 1.14 | CH$_3$ | CH$_3$ | — | Q$_2$ | C$_2$F$_5$ | — | CH$_3$ | m.p. = 125–128° |
| 1.15 | CH$_3$ | CH$_3$ | — | Q$_2$ | C$_3$F$_7$(n) | — | CH$_3$ | m.p. = 130–133° |
| 1.16 | CH$_3$ | CH$_3$ | — | Q$_2$ | C$_2$F$_5$ | — | C$_3$H$_7$(i) | m.p. = 146–149° |
| 1.17 | CH$_3$ | CH$_3$ | — | Q$_2$ | C$_3$F$_7$(n) | — | C$_3$H$_7$(i) | m.p. = 133–135° |
| 1.18 | C$_2$H$_5$ | C$_2$H$_5$ | — | Q$_2$ | CF$_3$ | — | C$_3$H$_7$(i) | m.p. = 128–130° |
| 1.19 | C$_2$H$_5$ | C$_2$H$_5$ | — | Q$_2$ | C$_2$F$_5$ | — | CH$_3$ | m.p. = 121–122° |
| 1.20 | C$_2$H$_5$ | C$_2$H$_5$ | — | Q$_2$ | C$_2$F$_5$ | — | C$_3$H$_7$(i) | m.p. = 106–108° |
| 1.21 | C$_2$H$_5$ | C$_2$H$_5$ | — | Q$_2$ | C$_3$F$_7$(n) | — | CH$_3$ | m.p. = 119–120° |
| 1.22 | C$_2$H$_5$ | C$_2$H$_5$ | — | Q$_2$ | C$_3$F$_7$(n) | — | C$_3$H$_7$(i) | m.p. = 113–114° |
| 1.23 | C$_2$H$_5$ | C$_2$H$_5$ | — | Q$_2$ | CF$_3$ | — | CH$_3$ | m.p. = 130–131° |
| 1.24 | C$_2$H$_5$ | C$_2$H$_5$ | — | Q$_3$ | C$_4$H$_9$(t) | — | — | m.p. = 128–130° |
| 1.25 | CH$_3$ | CH$_3$ | — | Q$_3$ | CF$_3$ | — | — | m.p. = 80–84° |
| 1.26 | CH$_3$ | CH$_3$ | — | Q$_4$ | CH$_3$ | — | — | m.p. = 128–130° |
| 1.27 | CH$_3$ | CH$_3$ | — | Q$_9$ | Cl | Cl | CH$_3$ | m.p. = 176.5–177° |
| 1.28 | C$_2$H$_5$ | C$_2$H$_5$ | — | Q$_9$ | Cl | Cl | CH$_3$ | m.p. = 120.5–121.5° |
| 1.29 | C$_3$H$_7$(i) | C$_3$H$_7$(i) | — | Q$_4$ | CH$_3$ | — | — | solid |
| 1.30 | CH$_3$ | CH$_3$ | — | Q$_1$ | Cl | CH$_3$ | — | $n_D^{23}$ = 1.6075 |
| 1.31 | C$_2$H$_5$ | C$_2$H$_5$ | — | Q$_1$ | Cl | CH$_3$ | — | $n_D^{25}$ = 1.5930 |
| 1.32 | C$_3$H$_7$(i) | C$_3$H$_7$(i) | — | Q$_1$ | Cl | Cl | — | dark oil* |
| 1.33 | CH$_3$ | CH$_3$ | — | Q$_8$ | Cl | Cl | — | m.p. = 166–170° |

*nmr (CDCl$_3$):
δ = 1.25 (d,12)
2.88 (septet, 2)
3.95 (broad, NH$_2$)
6.85 (s,2)

The following anilines of formula III' can also be prepared in analogous manner:

| R$_2$ | R$_3$ | R$_4$ | R$_5$ | R$_6$ | R$_7$ | R$_8$ |
|---|---|---|---|---|---|---|
| C$_3$H$_7$(i) | C$_3$H$_7$(i) | — | Q$_7$ | H | H | — |
| CH$_3$ | CH$_3$ | — | Q$_7$ | 6-Cl | H | — |
| C$_2$H$_5$ | C$_2$H$_5$ | — | Q$_7$ | 6-Cl | H | — |
| C$_3$H$_7$(i) | C$_3$H$_7$(i) | — | Q$_7$ | 6-Cl | H | — |
| CH$_3$ | CH$_3$ | — | Q$_8$ | 6-Cl | H | — |
| C$_2$H$_5$ | C$_2$H$_5$ | — | Q$_8$ | 6-Cl | H | — |
| C$_3$H$_7$(i) | C$_3$H$_7$(i) | — | Q$_8$ | 6-Cl | H | — |
| CH$_3$ | CH$_3$ | — | Q$_4$ | CF$_3$ | — | — |
| C$_2$H$_5$ | C$_2$H$_5$ | — | Q$_4$ | CF$_3$ | — | — |
| C$_3$H$_7$(i) | C$_3$H$_7$(i) | — | Q$_4$ | CF$_3$ | — | — |
| C$_3$H$_7$(i) | C$_3$H$_7$(i) | — | Q$_9$ | Cl | Cl | CH$_3$ |
| CH$_3$ | CH$_3$ | — | Q$_4$ | CF$_3$ | — | — |
| C$_2$H$_5$ | C$_2$H$_5$ | — | Q$_4$ | CF$_3$ | — | — |
| C$_3$H$_7$(i) | C$_3$H$_7$(i) | — | Q$_4$ | CF$_3$ | — | — |
| CH$_3$ | CH$_3$ | — | Q$_9$ | Cl | Cl | H |
| C$_2$H$_5$ | C$_2$H$_5$ | — | Q$_9$ | Cl | Cl | H |
| C$_3$H$_7$(i) | C$_3$H$_7$(i) | — | Q$_9$ | Cl | Cl | H |
| CH$_3$ | CH$_3$ | — | Q$_9$ | Br | Br | H |
| C$_2$H$_5$ | C$_2$H$_5$ | — | Q$_9$ | Br | Br | H |
| C$_3$H$_7$(i) | C$_3$H$_7$(i) | — | Q$_9$ | Br | Br | H |
| CH$_3$ | CH$_3$ | — | Q$_6$ | H | H | — |
| C$_2$H$_5$ | C$_2$H$_5$ | — | Q$_6$ | H | H | — |
| C$_2$H$_5$ | CH$_3$ | — | Q$_6$ | H | H | — |
| C$_3$H$_7$(i) | C$_3$H$_7$(i) | — | Q$_6$ | H | H | — |
| CH$_3$ | CH$_3$ | — | Q$_4$ | C$_6$H$_5$ | — | — |
| C$_2$H$_5$ | C$_2$H$_5$ | — | Q$_4$ | C$_6$H$_5$ | — | — |
| C$_3$H$_7$(i) | C$_3$H$_7$(i) | — | Q$_4$ | C$_6$H$_5$ | — | — |
| CH$_3$ | CH$_3$ | — | Q$_7$ | H | — | — |
| C$_2$H$_5$ | C$_2$H$_5$ | — | Q$_7$ | H | — | — |
| C$_2$H$_5$ | C$_2$H$_5$ | — | Q$_1$ | CF$_3$ | Br | — |
| C$_2$H$_5$ | C$_2$H$_5$ | — | Q$_4$ | CH$_3$ | — | — |
| CH$_3$ | CH$_3$ | — | Q$_3$ | C$_4$H$_9$(t) | — | — |
| CH$_3$ | CH$_3$ | — | Q$_5$ | C$_4$H$_9$(t) | — | — |
| C$_3$H$_7$(i) | C$_3$H$_7$(i) | — | Q$_1$ | Cl | CH$_3$ | — |
| CH$_3$ | CH$_3$ | — | Q$_1$ | CH$_3$ | Cl | — |
| C$_2$H$_5$ | C$_2$H$_5$ | — | Q$_1$ | CH$_3$ | Cl | — |
| C$_3$H$_7$(i) | C$_3$H$_7$(i) | — | Q$_1$ | CH$_3$ | Cl | — |

-continued

| R₂ | R₃ | R₄ | R₅ | R₆ | R₇ | R₈ |
|---|---|---|---|---|---|---|
| CH₃ | CH₃ | — | Q₁ | CH₃ | Br | — |
| C₂H₅ | C₂H₅ | — | Q₁ | CH₃ | Br | — |
| C₃H₇(i) | C₃H₇(i) | — | Q₁ | CH₃ | Br | — |
| CH₃ | CH₃ | — | Q₁ | CH₃ | CH₃ | — |
| C₂H₅ | C₂H₅ | — | Q₁ | CH₃ | CH₃ | — |
| C₃H₇(i) | C₃H₇(i) | — | Q₁ | CH₃ | CH₃ | — |
| CH₃ | CH₃ | — | Q₄ | C₂H₅ | — | — |
| C₂H₅ | C₂H₅ | — | Q₄ | C₂H₅ | — | — |
| C₃H₇(i) | C₃H₇(i) | — | Q₄ | C₂H₅ | — | — |
| CH₃ | CH₃ | — | Q₄ | C₃H₇(i) | — | — |
| C₂H₅ | C₂H₅ | — | Q₄ | C₃H₇(i) | — | — |
| C₃H₇(i) | C₃H₇(i) | — | Q₄ | C₃H₇(i) | — | — |

The following anilines of formula III are also prepared as described in Example 1:

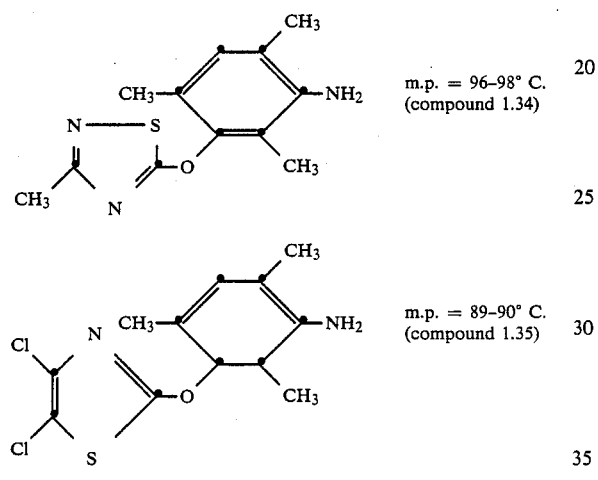

m.p. = 96–98° C. (compound 1.34)

m.p. = 89–90° C. (compound 1.35)

EXAMPLE 2

Preparation of 2,6-dimethyl-4-(4-bromo-1,3-thiazol-2-yloxy)phenylisothiocyanate

With stirring and cooling with ice, 4.5 g of 2,6-dimethyl-4-(4-bromo-1,3-thiazol-2-yloxy)aniline are added dropwise to a mixture of 15 ml of water, 30 ml of dichloromethane, 2.1 g of thiophosgene and 3.3 g of calcium carbonate. The reaction mixture is then heated to the boil for 2 hours, then cooled and filtered. The organic phase is separated and the aqueous phase is washed with dichloromethane, and the combined organic phases are dried over sodium sulfate. The solvent is removed by distillation, to give pale yellow crystals which are recrystallised from hexane.

The title compound of formula

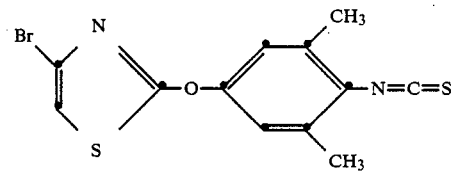

is isolated in the form of yellow crystals of m.p. 91.5°–93° C. (compound 2.01).

The following isothiocyanates of formula II′

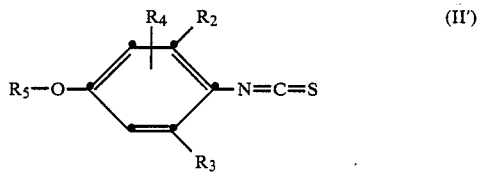

are prepared in accordance with the above procedure:

| Compound | R₂ | R₃ | R₄ | R₅ | R₆ | R₇ | R₈ | Physical data (°C.) |
|---|---|---|---|---|---|---|---|---|
| 2.01 | CH₃ | CH₃ | — | Q₁ | Br | H | — | m.p. = 91.5–93° |
| 2.02 | C₂H₅ | C₂H₅ | — | Q₁ | CF₃ | Br | — | m.p. = 82–86° |
| 2.03 | CH₃ | CH₃ | — | Q₁ | Br | Cl | — | m.p. = 76–77.4° |
| 2.04 | CH₃ | CH₃ | — | Q₁ | Br | Br | — | m.p. = 90–2° |
| 2.05 | CH₃ | CH₃ | — | Q₁ | Cl | Br | — | m.p. = 94.5–4° |
| 2.06 | CH₃ | CH₃ | — | Q₁ | Cl | Cl | — | m.p. = 73.5–4° |
| 2.07 | CH₃ | CH₃ | — | Q₁ | Cl | H | — | m.p. = 87–91° |
| 2.08 | CH₃ | CH₃ | — | Q₁ | CF₃ | H | — | m.p. = 102–3° |
| 2.09 | CH₃ | CH₃ | — | Q₁ | CF₃ | Br | — | m.p. = 113–15° |
| 2.10 | C₂H₅ | C₂H₅ | — | Q₁ | Cl | Cl | — | $n_D^{22}$ = 1.6410 |
| 2.11 | C₂H₅ | C₂H₅ | — | Q₁ | Cl | Br | — | m.p. = 47.5–9° |
| 2.12 | CH₃ | CH₃ | — | Q₂ | CF₃ | Br | CH₃ | oil |
| 2.13 | CH₃ | CH₃ | — | Q₂ | CF₃ | — | C₃H₇(i) | m.p. = 93–95 |
| 2.14 | CH₃ | CH₃ | — | Q₂ | C₂F₅ | — | CH₃ | m.p. = 85–86 |
| 2.15 | CH₃ | CH₃ | — | Q₂ | C₃F₇(n) | — | CH₃ | m.p. = 83–84 |
| 2.16 | CH₃ | CH₃ | — | Q₂ | C₂F₅ | — | C₃H₇(i) | m.p. = 72–74 |
| 2.17 | CH₃ | CH₃ | — | Q₂ | C₃F₇(n) | — | C₃H₇(i) | m.p. = 101–102 |
| 2.18 | C₂H₅ | C₂H₅ | — | Q₂ | C₃H₇(i) | — | C₃H₇(i) | m.p. = 83–84 |
| 2.19 | C₂H₅ | C₂H₅ | — | Q₂ | C₂F₅ | — | CH₃ | m.p. = 68–70 |
| 2.20 | C₂H₅ | C₂H₅ | — | Q₂ | C₂F₅ | — | C₃H₇(i) | m.p. = 42–43 |
| 2.21 | C₂H₅ | C₂H₅ | — | Q₂ | C₃F₇(n) | — | CH₃ | m.p. = 55–56 |
| 2.22 | C₂H₅ | C₂H₅ | — | Q₂ | C₃F₇(n) | — | C₃H₇(i) | oil |
| 2.23 | C₂H₅ | C₂H₅ | — | Q₂ | CF₃ | — | CH₃ | m.p. = 111–112 |
| 2.24 | C₂H₅ | C₂H₅ | — | Q₃ | C₄H₉(t) | — | — | m.p. = 97–98 |
| 2.25 | CH₃ | CH₃ | — | Q₃ | CF₃ | — | — | m.p. = 41–44 |
| 2.26 | CH₃ | CH₃ | — | Q₄ | CH₃ | — | — | oil |
| 2.27 | CH₃ | CH₃ | — | Q₉ | Cl | Cl | CH₃ | m.p. = 108.5–109 |
| 2.28 | C₂H₅ | C₂H₅ | — | Q₉ | Cl | Cl | CH₃ | m.p. = 110–111 |
| 2.29 | C₃H₇(i) | C₃H₇(i) | — | Q₄ | CH₃ | — | — | oil |
| 2.30 | CH₃ | CH₃ | — | Q₁ | Cl | CH₃ | — | m.p. = 112.5–113 |
| 2.31 | C₂H₅ | C₂H₅ | — | Q₁ | Cl | CH₃ | — | $n_D^{26}$ = 1.6300 |

-continued

| Compound | R2 | R3 | R4 | R5 | R6 | R7 | R8 | Physical data (°C.) |
|---|---|---|---|---|---|---|---|---|
| 2.32 | C3H7(i) | C3H7(i) | — | Q1 | Cl | Cl | — | Oel |
| 2.33 | CH3 | CH3 | — | Q8 | Cl | Cl | — | m.p. = 117–118.5° |

The following isothiocyanates of formula II' can be prepared as described above:

| R2 | R3 | R4 | R5 | R6 | R7 | R8 |
|---|---|---|---|---|---|---|
| CH3 | CH3 | — | Q3 | C4H9(t) | — | — |
| C3H7(n) | C3H7(n) | — | Q4 | CH3 | — | CH3 |
| CH3 | CH3 | — | Q5 | C4H9(t) | — | — |
| C2H5 | C2H5 | — | Q1 | CF3 | Br | — |
| C2H5 | CH3 | — | Q1 | CF3 | Br | — |
| CH3 | CH3 | — | Q6 | H | H | — |
| C2H5 | CH3 | — | Q6 | H | H | — |
| C2H5 | C2H5 | — | Q6 | H | H | — |
| C3H7(i) | C3H7(i) | — | Q6 | H | H | — |
| CH3 | CH3 | — | Q4 | C6H5 | — | — |
| C2H5 | C2H5 | — | Q4 | C6H5 | — | — |
| C3H7(i) | C3H7(i) | — | Q4 | C6H5 | — | — |
| CH3 | CH3 | — | Q7 | H | — | — |
| C2H5 | C2H5 | — | Q7 | H | — | — |
| C3H7(i) | C3H7(i) | — | Q7 | H | — | — |
| CH3 | CH3 | — | Q7 | 6-Cl | — | — |
| C2H5 | C2H5 | — | Q7 | 6-Cl | — | — |
| C3H7(i) | C3H7(i) | — | Q7 | 6-Cl | — | — |
| CH3 | CH3 | — | Q8 | 6-Cl | H | — |
| C2H5 | C2H5 | — | Q8 | 6-Cl | H | — |
| C3H7(i) | C3H7(i) | — | Q8 | 6-Cl | H | — |
| C2H5 | C2H5 | — | Q4 | CH3 | — | — |
| CH3 | CH3 | — | Q4 | CF3 | — | — |
| C2H5 | C2H5 | — | Q4 | CF3 | — | — |
| C3H7(i) | C3H7(i) | — | Q4 | CF3 | — | — |
| C3H7(i) | C3H7(i) | — | Q9 | Cl | Cl | CH3 |
| CH3 | CH3 | — | Q4 | CF3 | — | — |
| C2H5 | C2H5 | — | Q4 | CF3 | — | — |
| C3H7(i) | C3H7(i) | — | Q4 | CF3 | — | — |
| CH3 | CH3 | — | Q9 | Cl | Cl | H |
| C2H5 | C2H5 | — | Q9 | Cl | Cl | H |
| C3H7(i) | C3H7(i) | — | Q9 | Cl | Cl | H |
| CH3 | CH3 | — | Q9 | Br | Br | H |
| C2H5 | C2H5 | — | Q9 | Br | Br | H |
| C3H7(i) | C3H7(i) | — | Q9 | Br | Br | H |
| C3H7(i) | C3H7(i) | — | Q1 | Cl | CH3 | — |
| CH3 | CH3 | — | Q1 | CH3 | Cl | — |
| C2H5 | C2H5 | — | Q1 | CH3 | Cl | — |
| C3H7(i) | C3H7(i) | — | Q1 | CH3 | Cl | — |
| CH3 | CH3 | — | Q1 | CH3 | Br | — |
| C2H5 | C2H5 | — | Q1 | CH3 | Br | — |
| C3H7(i) | C3H7(i) | — | Q1 | CH3 | Br | — |
| CH3 | CH3 | — | Q1 | CH3 | CH3 | — |
| C2H5 | C2H5 | — | Q1 | CH3 | CH3 | — |
| C3H7(i) | C3H7(i) | — | Q1 | CH3 | CH3 | — |
| CH3 | CH3 | — | Q4 | C2H5 | — | — |
| C2H5 | C2H5 | — | Q4 | C2H5 | — | — |
| C3H7(i) | C3H7(i) | — | Q4 | C2H5 | — | — |
| CH3 | CH3 | — | Q4 | C3H7(i) | — | — |
| C2H5 | C2H5 | — | Q4 | C3H7(i) | — | — |
| C3H7(i) | C3H7(i) | — | Q4 | C3H7(i) | — | — |

The following isothiocyanates of formula II are also prepared as described in Example 2:

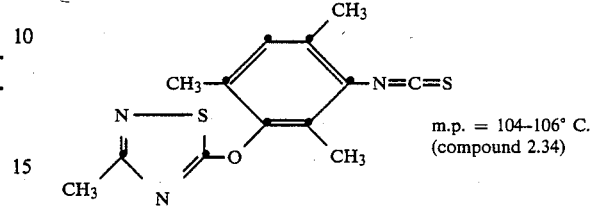

m.p. = 104–106° C. (compound 2.34)

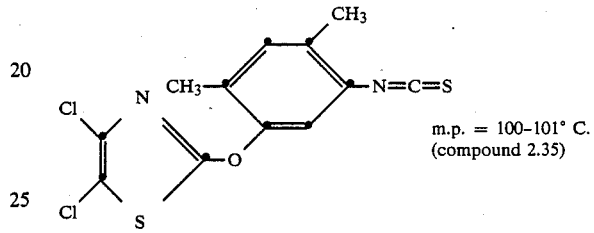

m.p. = 100–101° C. (compound 2.35)

EXAMPLE 3

Preparation of N-[2,6-dimethyl-4-(4-bromothiazol-2-yloxy)-phenyl]-N'-tert-butyl-thiorea 2.1 g of 2,6-dimethyl-4-(4-bromothiazol-2-yloxy)-phenylisothiocyanate and 0.7 g of tert-butylamine in 20 ml tetrahydrofuran are heated for 6 hours to 40° C. The batch is poured into 200 ml of ice-water and the precipitate is isolated by filtration. Recrystallisation of the precipitate from methanol affords the title compound of formula

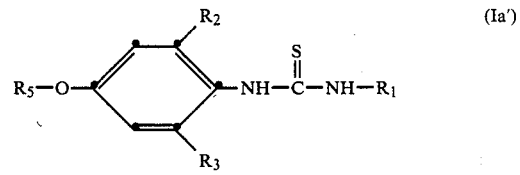

in crystalline form with a melting point of 143°–144° C. (compound 3.01).

The following thioureas of formula Ia' are prepared in accordance with the above described procedure:

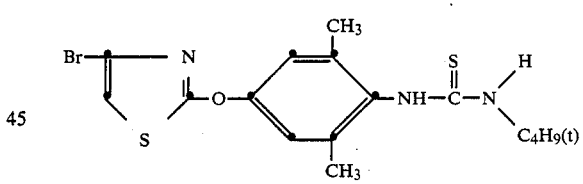

(Ia')

| Compound | R1 | R2 | R3 | R5 | R6 | R7 | R8 | Physical data (°C.) |
|---|---|---|---|---|---|---|---|---|
| 3.01 | C4H9(t) | CH3 | CH3 | Q1 | Br | H | — | m.p. = 143–144° |
| 3.02 | C4H9(t) | CH3 | CH3 | Q1 | CF3 | H | — | m.p. = 168–169° |
| 3.03 | C4H9(t) | CH3 | CH3 | Q1 | CF3 | Br | — | m.p. = 152–154° |
| 3.04 | (CH2)3OCH3 | CH3 | CH3 | Q1 | CF3 | Br | — | m.p. = 132–133° |

-continued

| Compound | R₁ | R₂ | R₃ | R₅ | R₆ | R₇ | R₈ | Physical data (°C.) |
|---|---|---|---|---|---|---|---|---|
| 3.05 | (cyclopentyl-H) | CH₃ | CH₃ | Q₁ | CF₃ | H | — | m.p. = 131–132° |
| 3.06 | (cyclopentyl-H) | CH₃ | CH₃ | Q₁ | CF₃ | Br | — | m.p. = 144–146° |
| 3.07 | (cyclohexyl-H) | CH₃ | CH₃ | Q₁ | CF₃ | H | — | m.p. = 165–166° |
| 3.08 | C₅H₁₁(t) | CH₃ | CH₃ | Q₁ | CF₃ | Br | — | m.p. = 110–114° |
| 3.09 | C₄H₉(t) | CH₃ | CH₃ | Q₁ | Cl | H | — | m.p. = 130–132° |
| 3.10 | C₄H₉(t) | CH₃ | CH₃ | Q₁ | Cl | Cl | — | m.p. = 120–123° |
| 3.11 | C₄H₉(t) | CH₃ | CH₃ | Q₁ | Cl | Br | — | m.p. = 157–159° |
| 3.12 | C₄H₉(t) | CH₃ | CH₃ | Q₁ | Br | Br | — | m.p. = 163–165° |
| 3.13 | C₅H₁₁(t) | CH₃ | CH₃ | Q₁ | Br | H | — | m.p. = 144–146° |
| 3.14 | C₄H₉(t) | C₂H₅ | C₂H₅ | Q₁ | CF₃ | Br | — | m.p. = 150–151.5° |
| 3.15 | C₄H₉(t) | CH₃ | CH₃ | Q₁ | Br | Cl | — | m.p. = 142–144° |
| 3.16 | C₄H₉(t) | C₂H₅ | C₂H₅ | Q₁ | Cl | Cl | — | m.p. = 114–116.5° |
| 3.17 | C₄H₉(t) | C₂H₅ | C₂H₅ | Q₁ | Cl | Br | — | m.p. = 139–141° |
| 3.18 | C₄H₉(t) | CH₃ | CH₃ | Q₂ | CF₃ | — | CH₃ | m.p. = 169–171° |
| 3.19 | C₄H₉(t) | CH₃ | CH₃ | Q₂ | CF₃ | — | C₃H₇(i) | m.p. = 184–185° |
| 3.20 | C₄H₉(t) | CH₃ | CH₃ | Q₂ | C₂F₅ | — | CH₃ | m.p. = 135–136° |
| 3.21 | C₄H₉(t) | CH₃ | CH₃ | Q₂ | C₃F₇(n) | — | CH₃ | m.p. = 116–118° |
| 3.22 | C₄H₉(t) | CH₃ | CH₃ | Q₃ | C₄H₉(t) | — | — | m.p. = 158–160° |
| 3.23 | C₄H₉(t) | C₂H₅ | C₂H₅ | Q₉ | Cl | Cl | CH₃ | m.p. = 146–147.5° |
| 3.24 | C₄H₉(t) | CH₃ | CH₃ | Q₉ | Cl | Cl | CH₃ | m.p. = 162–163° |
| 3.25 | (cyclopentyl) | C₂H₅ | C₂H₅ | Q₁ | Cl | Cl | — | m.p. = 125–127° |
| 3.26 | (cyclopentyl) | C₂H₅ | C₂H₅ | Q₁ | Cl | Br | — | m.p. = 157–159° |
| 3.27 | C₄H₉(t) | CH₃ | CH₃ | Q₅ | C₄H₉(t) | — | — | m.p. = 168–170° |
| 3.28 | C₄H₉(t) | CH₃ | CH₃ | Q₂ | C₂F₅ | — | C₃H₇(i) | m.p. = 151–152° |
| 3.29 | C₄H₉(t) | CH₃ | CH₃ | Q₂ | C₃F₇(n) | — | C₃H₇(i) | m.p. = 114–116° |
| 3.30 | C₄H₉(t) | C₂H₅ | C₂H₅ | Q₂ | CF₃ | — | C₃H₇(i) | m.p. = 163–165° |
| 3.31 | C₄H₉(t) | C₂H₅ | C₂H₅ | Q₂ | C₂F₅ | — | CH₃ | m.p. = 114–115° |
| 3.32 | C₄H₉(t) | C₂H₅ | C₂H₅ | Q₂ | C₂F₅ | — | C₃H₇(i) | m.p. = 155–156° |
| 3.33 | C₄H₉(t) | C₂H₅ | C₂H₅ | Q₂ | C₃F₇(n) | — | CH₃ | m.p. = 105–106° |
| 3.34 | C₄H₉(t) | C₂H₅ | C₂H₅ | Q₂ | C₃F₇(n) | — | C₃H₇(i) | m.p. = 130–131° |
| 3.35 | C₄H₉(t) | C₂H₅ | C₂H₅ | Q₂ | CF₃ | — | CH₃ | m.p. = 145–146° |
| 3.36 | C₄H₉(t) | C₂H₅ | C₂H₅ | Q₃ | C₄H₉(t) | — | — | m.p. = 147–149° |
| 3.37 | C₄H₉(t) | CH₃ | CH₃ | Q₃ | CF₃ | — | — | m.p. = 118–120° |
| 3.38 | C₃H₇(i) | CH₃ | CH₃ | Q₃ | CF₃ | — | — | m.p. = 103–106° |
| 3.39 | C₄H₉(t) | CH₃ | CH₃ | Q₄ | CH₃ | — | — | m.p. = 152–154° |
| 3.40 | C₃H₇(i) | CH₃ | CH₃ | Q₄ | CH₃ | — | — | m.p. = 163–165° |
| 3.41 | C₄H₉(t) | CH₃ | CH₃ | Q₉ | Cl | Cl | CH₃ | m.p. = 162–163° |
| 3.42 | C₄H₉(t) | C₂H₅ | C₂H₅ | Q₉ | Cl | Cl | CH₃ | m.p. = 146–147.5° |
| 3.43 | C₄H₉(t) | C₃H₇(i) | C₃H₇(i) | Q₄ | CH₃ | — | — | m.p. = 128–130° |
| 3.44 | C₄H₉(t) | CH₃ | CH₃ | Q₁ | Cl | CH₃ | — | m.p. = 145–147° |
| 3.45 | C₄H₉(t) | C₂H₅ | C₂H₅ | Q₁ | Cl | CH₃ | — | m.p. = 113.5–115.5° |
| 3.46 | C₄H₉(t) | C₃H₇(i) | C₃H₇(i) | Q₁ | Cl | Cl | — | m.p. = 120–124° |
| 3.47 | (cyclopentyl-H) | C₃H₇(i) | C₃H₇(i) | Q₁ | Cl | Cl | — | m.p. = 46–148.5° |
| 3.48 | C₄H₉(t) | CH₃ | CH₃ | Q₈ | 6-Cl | 5-Cl | — | m.p. = 174–176° |

-continued

| Compound | R₁ | R₂ | R₃ | R₅ | R₆ | R₇ | R₈ | Physical data (°C.) |
|---|---|---|---|---|---|---|---|---|
| 3.49 | $C_3H_7(i)$ | $CH_3$ | $CH_3$ | $Q_8$ | 6-Cl | 5-Cl | — | m.p. = 199–200° |

The following thioureas of formula Ia' can be prepared as described above:

| R₁ | R₂ | R₃ | R₅ | R₆ | R₇ | R₈ |
|---|---|---|---|---|---|---|
| $C_5H_{11}(t)$ | $CH_3$ | $CH_3$ | $Q_1$ | Cl | H | — |
| $C_5H_{11}(t)$ | $CH_3$ | $CH_3$ | $Q_1$ | Cl | Cl | — |
| $C_5H_{11}(t)$ | $CH_3$ | $CH_3$ | $Q_1$ | Cl | Br | — |
| $C_5H_{11}(t)$ | $CH_3$ | $CH_3$ | $Q_1$ | Br | Br | — |
| $C_5H_{11}(t)$ | $C_2H_5$ | $C_2H_5$ | $Q_1$ | $CF_3$ | Br | — |
| $CH(iC_3H_7)_2$ | $CH_3$ | $CH_3$ | $Q_1$ | $CF_3$ | Br | — |
| $C_4H_9(t)$ | $C_2H_5$ | $CH_3$ | $Q_1$ | $CF_3$ | Br | — |
| CH(cyclopropyl)₂ | $CH_3$ | $CH_3$ | $Q_1$ | $CF_3$ | Br | — |
| $C_4H_9(t)$ | $C_2H_5$ | $C_2H_5$ | $Q_4$ | $CH_3$ | — | — |
| $C_4H_9(t)$ | $C_3H_7(i)$ | $C_3H_7(i)$ | $Q_1$ | Cl | $CH_3$ | — |
| $C_5H_{11}(t)$ | $C_2H_5$ | $C_2H_5$ | $Q_1$ | Cl | Cl | — |
| $C_4H_9(s)$ | $C_2H_5$ | $C_2H_5$ | $Q_1$ | Cl | Cl | — |
| $C_3H_7(i)$ | $C_2H_5$ | $C_2H_5$ | $Q_1$ | Cl | Cl | — |
| cyclopentyl | $CH_3$ | $CH_3$ | $Q_1$ | Cl | $CH_3$ | — |
| cyclopentyl | $C_2H_5$ | $C_2H_5$ | $Q_1$ | Cl | $CH_3$ | — |
| $C_5H_{11}(t)$ | $CH_3$ | $CH_3$ | $Q_1$ | Cl | $CH_3$ | — |
| $C_5H_{11}(t)$ | $C_2H_5$ | $C_2H_5$ | $Q_1$ | Cl | $CH_3$ | — |
| $C_5H_{11}(t)$ | $C_3H_7(i)$ | $C_3H_7(i)$ | $Q_1$ | Cl | $CH_3$ | — |
| $C_3H_7(i)$ | $C_2H_5$ | $C_2H_5$ | $Q_1$ | Cl | $CH_3$ | — |

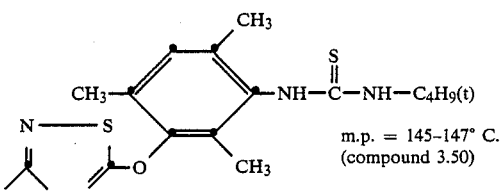

m.p. = 145–147° C. (compound 3.50)

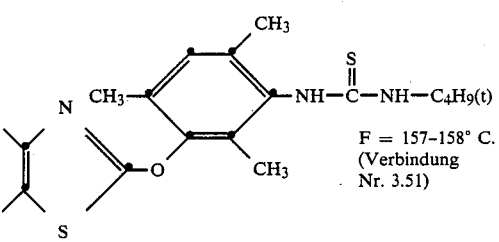

F = 157–158° C. (Verbindung Nr. 3.51)

EXAMPLE 4

Preparation of N-[2,6-dimethyl-4-(4-trifluoromethylthiazol-2-yloxy)-phenyl]-N'-tert-butyl-S-methylisothiourea 5 g of N-[2,6-dimethyl-4-(4-trifluoromethylthiazol-2-yloxy)phenyl]-N'-tert-butylthiourea are heated in 30 ml of ethanol and 2.1 g of iodomethane for 5 hours to 50° C. The alcohol is subsequently removed by evaporation and the residue is taken up in methylene chloride. The methylene chloride solution is washed twice with dilute sodium carbonate solution and dried over sodium sulfate. The solvent is removed by evaporation and the residue is recrystallised from hexane, affording the title compound of formula

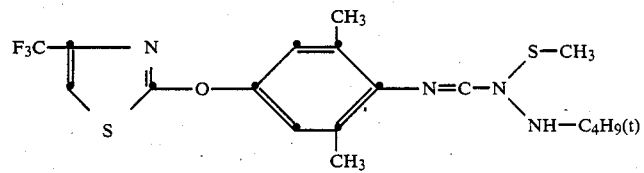

with a melting point of 88°–90° C. (compound 4.01).

The following compounds of formula Ib' are prepared in accordance with the procedure described above:

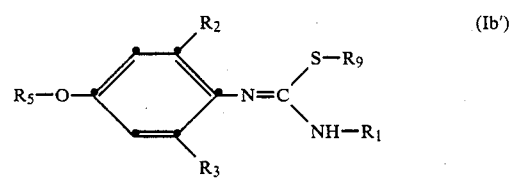

(Ib')

| Compound | R₁ | R₂ | R₃ | R₅ | R₆ | R₇ | R₈ | R₉ | Physical data (°C.) | Salt form |
|---|---|---|---|---|---|---|---|---|---|---|
| 4.01 | $C_4H_9(t)$ | $CH_3$ | $CH_3$ | $Q_1$ | $CF_3$ | H | — | $CH_3$ | m.p. = 88–90° | — |

-continued

| Compound | $R_1$ | $R_2$ | $R_3$ | $R_5$ | $R_6$ | $R_7$ | $R_8$ | $R_9$ | Physical data (°C.) | Salt form |
|---|---|---|---|---|---|---|---|---|---|---|
| 4.02 | $C_4H_9(t)$ | $CH_3$ | $CH_3$ | $Q_1$ | $CF_3$ | Br | — | $CH_3$ | m.p. = 102–104° | — |
| 4.03 | $(CH_2)_3$—$OCH_3$ | $CH_3$ | $CH_3$ | $Q_1$ | $CF_3$ | Br | — | $CH_3$ | m.p. 53–54° | — |
| 4.04 | $C_4H_9(t)$ | $CH_3$ | $CH_3$ | $Q_1$ | $CF_3$ | Br | — | $C_2H_5$ | m.p. = 89–91° | — |
| 4.05 | cyclopentyl | $CH_3$ | $CH_3$ | $Q_1$ | $CF_3$ | Br | — | $CH_3$ | m.p. = 109–111° | — |
| 4.06 | cyclopentyl | $CH_3$ | $CH_3$ | $Q_1$ | $CF_3$ | H | — | $CH_3$ | m.p. = 80–81° | — |
| 4.07 | cyclopentyl | $CH_3$ | $CH_3$ | $Q_1$ | $CF_3$ | H | — | $C_2H_5$ | m.p. = 75–76° | — |
| 4.08 | cyclohexyl | $CH_3$ | $CH_3$ | $Q_1$ | $CF_3$ | H | — | $CH_3$ | m.p. = 80–81° | — |
| 4.09 | cyclohexyl | $CH_3$ | $CH_3$ | $Q_1$ | $CF_3$ | H | — | $C_2H_5$ | m.p. = 54–56° | — |
| 4.10 | $C_5H_{11}(t)$ | $CH_3$ | $CH_3$ | $Q_1$ | $CF_3$ | Br | — | $CH_3$ | m.p. = 76–78° | — |
| 4.11 | $C_5H_{11}(t)$ | $CH_3$ | $CH_3$ | $Q_1$ | $CF_3$ | Br | — | $C_2H_5$ | m.p. 78–80° | — |
| 4.12 | $C_4H_9(t)$ | $CH_3$ | $CH_3$ | $Q_1$ | Cl | H | — | $CH_3$ | m.p. = 105–107° | — |
| 4.13 | $C_4H_9(t)$ | $CH_3$ | $CH_3$ | $Q_1$ | Cl | H | — | $C_2H_5$ | m.p. = 101–103° | — |
| 4.14 | $C_4H_9(t)$ | $CH_3$ | $CH_3$ | $Q_1$ | Br | H | — | $CH_3$ | m.p. = 94–96° | — |
| 4.15 | $C_4H_9(t)$ | $CH_3$ | $CH_3$ | $Q_1$ | Br | H | — | $C_2H_5$ | m.p. = 105.5–107° | — |
| 4.16 | $C_4H_9(t)$ | $CH_3$ | $CH_3$ | $Q_1$ | Cl | Cl | — | $CH_3$ | m.p. = 106.5–108° | — |
| 4.17 | $C_4H_9(t)$ | $CH_3$ | $CH_3$ | $Q_1$ | Cl | Br | — | $CH_3$ | m.p. = 123–125° C. | — |
| 4.18 | $C_4H_9(t)$ | $CH_3$ | $CH_3$ | $Q_1$ | Br | Br | — | $CH_3$ | m.p. = 130.5–132° | — |
| 4.19 | $C_4H_9(t)$ | $C_2H_5$ | $C_2H_5$ | $Q_1$ | $CF_3$ | Br | — | $CH_3$ | m.p. = 92–94° | — |
| 4.20 | $C_4H_9(t)$ | $C_2H_5$ | $C_2H_5$ | $Q_1$ | Cl | Cl | — | $CH_3$ | m.p. = 77.5–79° | — |
| 4.21 | $C_4H_9(t)$ | $C_2H_5$ | $C_2H_5$ | $Q_1$ | Cl | Br | — | $CH_3$ | m.p. = 77.5–79° | — |
| 4.22 | $C_4H_9(t)$ | $CH_3$ | $CH_3$ | $Q_1$ | Br | Cl | — | $CH_3$ | m.p. = 117–119° | — |
| 4.23 | cyclopentyl | $CH_3$ | $CH_3$ | $Q_1$ | $CF_3$ | Br | — | $C_2H_5$ | m.p. = 90–92° | — |
| 4.24 | $C_4H_9(t)$ | $C_2H_5$ | $C_2H_5$ | $Q_1$ | $CF_3$ | Br | — | $CH_3$ | m.p. = 167–170° | HI |
| 4.25 | $C_4H_9(t)$ | $CH_3$ | $CH_3$ | $Q_1$ | Br | Cl | — | $CH_3$ | m.p. = 193–195° | HI |
| 4.26 | $C_4H_9(t)$ | $CH_3$ | $CH_3$ | $Q_1$ | Br | H | — | $CH_3$ | m.p. = 179–180° | HI |
| 4.27 | $C_4H_9(t)$ | $CH_3$ | $CH_3$ | $Q_1$ | Cl | Br | — | $CH_3$ | m.p. = 191–192.5° | HI |
| 4.28 | $C_4H_9(t)$ | $CH_3$ | $CH_3$ | $Q_1$ | Cl | Cl | — | $CH_3$ | m.p. = 175–177° | HI |
| 4.29 | $C_4H_9(t)$ | $CH_3$ | $CH_3$ | $Q_1$ | Br | Br | — | $CH_3$ | m.p. = 199–201° | HI |
| 4.30 | $C_4H_9(t)$ | $C_2H_5$ | $C_2H_5$ | $Q_1$ | Cl | Cl | — | $C_2H_5$ | $n_D^{24}$ = 1.580 | — |
| 4.31 | $C_4H_9(t)$ | $C_2H_5$ | $C_2H_5$ | $Q_1$ | Cl | Br | — | $C_2H_5$ | $n_D^{24}$ = 1.586 | — |
| 4.32 | $C_4H_9(t)$ | $C_2H_5$ | $C_2H_5$ | $Q_1$ | Cl | Br | — | $C_2H_5$ | m.p. = 177.5–180° | HI |
| 4.33 | $C_4H_9(t)$ | $C_2H_5$ | $C_2H_5$ | $Q_1$ | Cl | Cl | — | $C_2H_5$ | m.p. = 170–172.5° | HI |
| 4.34 | $C_4H_9(t)$ | $C_2H_5$ | $C_2H_5$ | $Q_1$ | Cl | Br | — | $CH_3$ | m.p. = 191.5–194° | HI |
| 4.35 | $C_4H_9(t)$ | $C_2H_5$ | $C_2H_5$ | $Q_1$ | Cl | Cl | — | $CH_3$ | m.p. = 187–190° | HI |
| 4.36 | $C_4H_9(t)$ | $CH_3$ | $CH_3$ | $Q_9$ | Cl | Cl | $CH_3$ | $CH_3$ | m.p. = 162–163.5° | — |
| 4.37 | $C_4H_9(t)$ | $CH_3$ | $CH_3$ | $Q_9$ | Cl | Cl | $CH_3$ | $CH_3$ | m.p. = 183.5–185° | HI |
| 4.38 | $C_4H_9(t)$ | $C_2H_5$ | $C_2H_5$ | $Q_9$ | Cl | Cl | $CH_3$ | $CH_3$ | m.p. = 81.5–83° | — |
| 4.39 | $C_4H_9(t)$ | $C_2H_5$ | $C_2H_5$ | $Q_9$ | Cl | Cl | $CH_3$ | $CH_3$ | m.p. = 154.5–156° | HI |
| 4.40 | cyclopentyl | $C_2H_5$ | $C_2H_5$ | $Q_1$ | Cl | Cl | — | $CH_3$ | m.p. = 53–54° | — |

-continued

| Compound | R$_1$ | R$_2$ | R$_3$ | R$_5$ | R$_6$ | R$_7$ | R$_8$ | R$_9$ | Physical data (°C.) | Salt form |
|---|---|---|---|---|---|---|---|---|---|---|
| 4.41 | cyclopentyl-H | C$_2$H$_5$ | C$_2$H$_5$ | Q$_1$ | Cl | Cl | — | CH$_3$ | m.p. = 190–192° | HI |
| 4.42 | cyclopentyl-H | C$_2$H$_5$ | C$_2$H$_5$ | Q$_1$ | Cl | Cl | — | C$_2$H$_5$ | $n_D^{23}$ = 1.5852 | — |
| 4.43 | cyclopentyl-H | C$_2$H$_5$ | C$_2$H$_5$ | Q$_1$ | Cl | Cl | — | C$_2$H$_5$ | m.p. = 187–188° | HI |
| 4.44 | cyclopentyl-H | C$_2$H$_5$ | C$_2$H$_5$ | Q$_1$ | Cl | Br | — | CH$_3$ | m.p. = 66–67° | — |
| 4.45 | cyclopentyl-H | C$_2$H$_5$ | C$_2$H$_5$ | Q$_1$ | Cl | Br | — | CH$_3$ | m.p. = 190–192° | HI |
| 4.46 | cyclopentyl-H | C$_2$H$_5$ | C$_2$H$_5$ | Q$_1$ | Cl | Br | — | C$_2$H$_5$ | m.p. = 47.5–49° | — |
| 4.47 | cyclopentyl-H | C$_2$H$_5$ | C$_2$H$_5$ | Q$_1$ | Cl | Br | — | C$_2$H$_5$ | m.p. = 193–195° | HI |
| 4.48 | C$_4$H$_9$(t) | CH$_3$ | CH$_3$ | Q$_2$ | CF$_3$ | — | CH$_3$ | CH$_3$ | m.p. = 92–93° | — |
| 4.49 | C$_4$H$_9$(t) | CH$_3$ | CH$_3$ | Q$_2$ | CF$_3$ | — | C$_3$H$_7$(i) | CH$_3$ | m.p. = 179–180° | — |
| 4.50 | C$_4$H$_9$(t) | CH$_3$ | CH$_3$ | Q$_2$ | C$_2$F$_5$ | — | CH$_3$ | CH$_3$ | m.p. = 88–89° | — |
| 4.51 | C$_4$H$_9$(t) | CH$_3$ | CH$_3$ | Q$_2$ | C$_2$F$_5$ | — | C$_3$H$_7$(i) | CH$_3$ | m.p. = 140–144° | — |
| 4.52 | C$_4$H$_9$(t) | CH$_3$ | CH$_3$ | Q$_2$ | C$_3$F$_7$(n) | — | CH$_3$ | CH$_3$ | m.p. = 79–80° | — |
| 4.53 | C$_4$H$_9$(t) | C$_2$H$_5$ | C$_2$H$_5$ | Q$_2$ | C$_3$F$_7$(n) | — | CH$_3$ | CH$_3$ | oil | — |
| 4.54 | C$_4$H$_9$(t) | C$_2$H$_5$ | C$_2$H$_5$ | Q$_2$ | CF$_3$ | — | CH$_3$ | CH$_3$ | m.p. = 95–96° | — |
| 4.55 | C$_4$H$_9$(t) | C$_2$H$_5$ | C$_2$H$_5$ | Q$_2$ | CF$_3$ | — | C$_3$H$_7$(i) | CH$_3$ | m.p. = 127–128° | — |
| 4.56 | C$_4$H$_9$(t) | C$_2$H$_5$ | C$_2$H$_5$ | Q$_2$ | C$_2$F$_5$ | — | CH$_3$ | CH$_3$ | m.p. = 77–78° | — |
| 4.57 | C$_4$H$_9$(t) | C$_2$H$_5$ | C$_2$H$_5$ | Q$_2$ | C$_2$F$_5$ | — | C$_3$H$_7$(i) | CH$_3$ | m.p. = 112–113° | — |
| 4.58 | C$_4$H$_9$(t) | CH$_3$ | CH$_3$ | Q$_2$ | C$_3$F$_7$(n) | — | C$_3$H$_7$(i) | CH$_3$ | m.p. = 96–97° | — |
| 4.59 | C$_4$H$_9$(t) | C$_2$H$_5$ | C$_2$H$_5$ | Q$_2$ | C$_3$F$_7$(n) | — | C$_3$H$_7$(i) | CH$_3$ | m.p. = 80–81° | — |
| 4.60 | C$_4$H$_9$(t) | CH$_3$ | CH$_3$ | Q$_3$ | CF$_3$ | — | — | CH$_3$ | m.p. = 83–85° | — |
| 4.61 | C$_3$H$_7$(i) | CH$_3$ | CH$_3$ | Q$_3$ | CF$_3$ | — | — | CH$_3$ | m.p. = 92–94° | — |
| 4.62 | C$_4$H$_9$(t) | C$_3$H$_7$(i) | C$_3$H$_7$(i) | Q$_4$ | CH$_3$ | — | — | CH$_3$ | m.p. = 93–95° | — |
| 4.63 | C$_4$H$_9$(t) | CH$_3$ | CH$_3$ | Q$_1$ | Cl | CH$_3$ | — | CH$_3$ | m.p. = 127.5–129° | — |
| 4.64 | C$_4$H$_9$(t) | CH$_3$ | CH$_3$ | Q$_1$ | Cl | CH$_3$ | — | CH$_3$ | m.p. = 162–166° | HI |
| 4.65 | C$_4$H$_9$(t) | C$_2$H$_5$ | C$_2$H$_5$ | Q$_1$ | Cl | CH$_3$ | — | CH$_3$ | m.p. = 83–84° | — |
| 4.66 | C$_4$H$_9$(t) | C$_2$H$_5$ | C$_2$H$_5$ | Q$_1$ | Cl | CH$_3$ | — | CH$_3$ | m.p. = 165–168° | HI |
| 4.67 | C$_4$H$_9$(t) | C$_3$H$_7$(i) | C$_3$H$_7$(i) | Q$_1$ | Cl | Cl | — | CH$_3$ | m.p. = 93–97° | HI |
| 4.68 | C$_4$H$_9$(t) | C$_3$H$_7$(i) | C$_3$H$_7$(i) | Q$_1$ | Cl | Cl | — | CH$_3$ | $n_D^{27}$ = 1.5608 | — |
| 4.69 | cyclopentyl-H | C$_3$H$_7$(i) | C$_3$H$_7$(i) | Q$_1$ | Cl | Cl | — | CH$_3$ | m.p. = 170–174° | HI |
| 4.70 | cyclopentyl-H | C$_3$H$_7$(i) | C$_3$H$_7$(i) | Q$_1$ | Cl | Cl | — | CH$_3$ | m.p. = 93–96,5° | — |
| 4.71 | C$_4$H$_9$(t) | CH$_3$ | CH$_3$ | Q$_8$ | 6-Cl | 5-Cl | — | CH$_3$ | m.p. = 160–164°* | HI |
| 4.72 | C$_4$H$_9$(t) | CH$_3$ | CH$_3$ | Q$_8$ | 6-Cl | 5-Cl | — | CH$_3$ | m.p. = 98–104°* | — |

-continued

| Compound | R₁ | R₂ | R₃ | R₅ | R₆ | R₇ | R₈ | R₉ | Physical data (°C.) | Salt form |
|---|---|---|---|---|---|---|---|---|---|---|
| 4.73 | $C_3H_7(i)$ | $CH_3$ | $CH_3$ | $Q_8$ | 6-Cl | 5-Cl | — | $CH_3$ | m.p. = 187–191°* | HI |
| 4.74 | $C_3H_7(i)$ | $CH_3$ | $CH_3$ | $Q_8$ | 6-Cl | 5-Cl | — | $CH_3$ | m.p. = 160–163.5°* | — |

*contains small amounts of further isomers

The following isothioureas of formula Ib' can also be prepared as described above:

| R₁ | R₂ | R₃ | R₅ | R₆ | R₇ | R₈ | R₉ |
|---|---|---|---|---|---|---|---|
| $C_4H_9(t)$ | $CH_3$ | $CH_3$ | $Q_1$ | Cl | Cl | — | $C_2H_5$ |
| $C_4H_9(t)$ | $CH_3$ | $CH_3$ | $Q_1$ | Cl | Br | — | $C_2H_5$ |
| $C_4H_9(t)$ | $CH_3$ | $CH_3$ | $Q_1$ | Br | Br | — | $C_2H_5$ |
| $C_5H_{11}(t)$ | $CH_3$ | $CH_3$ | $Q_1$ | Cl | H | — | $CH_3$ |
| $C_5H_{11}(t)$ | $CH_3$ | $CH_3$ | $Q_1$ | Cl | Cl | — | $CH_3$ |
| $C_5H_{11}(t)$ | $CH_3$ | $CH_3$ | $Q_1$ | Cl | Br | — | $CH_3$ |
| $C_5H_{11}(t)$ | $CH_3$ | $CH_3$ | $Q_1$ | Br | H | — | $CH_3$ |
| $C_5H_{11}(t)$ | $CH_3$ | $CH_3$ | $Q_1$ | Br | Br | — | $CH_3$ |
| $C_4H_9(t)$ | $C_2H_5$ | $C_2H_5$ | $Q_1$ | $CF_3$ | Br | — | $C_2H_5$ |
| $C_5H_{11}(t)$ | $C_2H_5$ | $C_2H_5$ | $Q_1$ | $CF_3$ | Br | — | $CH_3$ |
| $CH(i-C_3H_7)_2$ | $CH_3$ | $CH_3$ | $Q_1$ | $CF_3$ | Br | — | $CH_3$ |
| 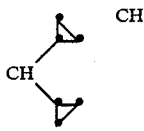 | $CH_3$ | $CH_3$ | $Q_1$ | $CF_3$ | Br | — | $CH_3$ |
| $C_4H_9(t)$ | $C_2H_5$ | $C_2H_5$ | $Q_4$ | $CH_3$ | — | — | $CH_3$ |
| $C_4H_9(t)$ | $C_2H_5$ | $C_2H_5$ | $Q_4$ | $CH_3$ | — | — | $C_2H_5$ |
| $C_4H_9(t)$ | $C_3H_7(i)$ | $C_3H_7(i)$ | $Q_1$ | Cl | $CH_3$ | — | $CH_3$ |
| $C_5H_{11}(t)$ | $C_2H_5$ | $C_2H_5$ | $Q_1$ | Cl | Cl | — | $CH_3$ |
| $C_4H_9(s)$ | $C_2H_5$ | $C_2H_5$ | $Q_1$ | Cl | Cl | — | $CH_3$ |
| $C_3H_7(i)$ | $C_2H_5$ | $C_2H_5$ | $Q_1$ | Cl | Cl | — | $CH_3$ |
| cyclopentyl | $CH_3$ | $CH_3$ | $Q_1$ | Cl | $CH_3$ | — | $CH_3$ |
| cyclopentyl | $C_2H_5$ | $C_2H_5$ | $Q_1$ | Cl | $CH_3$ | — | $CH_3$ |
| $C_5H_{11}(t)$ | $CH_3$ | $CH_3$ | $Q_1$ | Cl | $CH_3$ | — | $CH_3$ |
| $C_5H_{11}(t)$ | $C_2H_5$ | $C_2H_5$ | $Q_1$ | Cl | $CH_3$ | — | $CH_3$ |
| $C_9H_{11}(t)$ | $C_3H_7(i)$ | $C_3H_7(i)$ | $Q_1$ | Cl | $CH_3$ | — | $CH_3$ |
| $C_3H_7(t)$ | $C_2H_5$ | $C_2H_5$ | $Q_1$ | Cl | $CH_3$ | — | $CH_3$ |
| $C_4H_9(t)$ | $CH_3$ | $CH_3$ | $Q_1$ | Br | $CH_3$ | — | $CH_3$ |
| $C_4H_9(t)$ | $C_2H_5$ | $C_2H_5$ | $Q_1$ | Br | $CH_3$ | — | $CH_3$ |
| $C_4H_9(t)$ | $C_3H_7(i)$ | $C_3H_7(i)$ | $Q_1$ | Br | $CH_3$ | — | $CH_3$ |
| $C_4H_9(t)$ | $CH_3$ | $CH_3$ | $Q_1$ | $CH_3$ | $CH_3$ | — | $CH_3$ |
| $C_4H_9(t)$ | $C_2H_5$ | $C_2H_5$ | $Q_1$ | $CH_3$ | $CH_3$ | — | $CH_3$ |
| $C_4H_9(t)$ | $CH_3$ | $CH_3$ | $Q_4$ | $C_2H_5$ | — | — | $CH_3$ |
| $C_4H_9(t)$ | $C_2H_5$ | $C_2H_5$ | $Q_4$ | $C_2H_5$ | — | — | $CH_3$ |
| $C_4H_9(t)$ | $CH_3$ | $CH_3$ | $Q_4$ | $C_3H_7(i)$ | — | — | $CH_3$ |
| $C_4H_9(t)$ | $C_2H_5$ | $C_2H_5$ | $Q_4$ | $C_3H_7(i)$ | — | — | $CH_3$ |

The following isothiourea falling under formula Ib can also be obtained according to the process of Example 4:

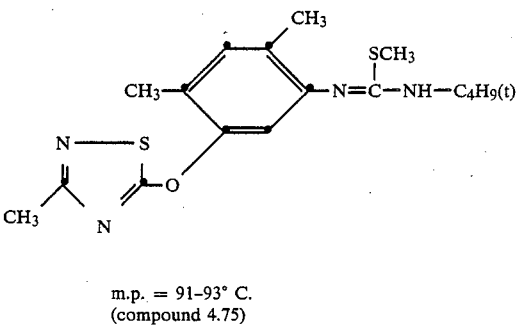

m.p. = 91–93° C.
(compound 4.75)

EXAMPLE 5

Preparation of N-[2,6-diethyl-4-(4,5-dichlorothiazol-2-yl)oxy]phenyl-N'-(tert-butyl)carbodiimide 5.0 g N-[2,6-diethyl-4-(4,5-dichlorothiazol-2-yl)oxy]-phenyl-N'-(tert-butyl)thiourea and 3.55 g 2-chloro-1-methylpyridinium iodide are added to 35 ml of dry acetonitrile and 2.8 g of triethylamine in 50 ml of acetonitrile are added dropwise at reflux temperature. The reaction mixture is stirred under reflux for a further 25 hours, the solvent is removed under vacuum and the residue is taken up in hexane. Insoluble matter is removed by filtration and the filtrate is washed three times with water, dried over $Na_2SO_4$, and the solvent is removed under vacuum.

The title compound of formula

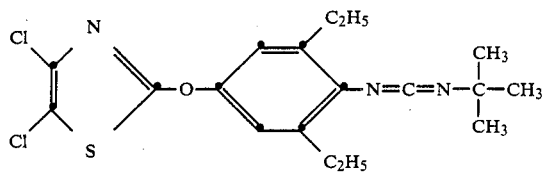

is isolated in the form of a yellow oil with a refractive index of $n_D^{24} = 1.5783$ (compound 5.09).

The following carbodiimides of formula Ic' are prepared in accordance with the procedure described above:

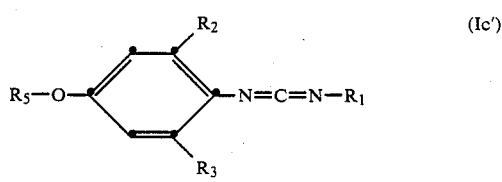

(Ic')

| Compound | R₁ | R₂ | R₃ | R₅ | R₆ | R₇ | R₈ | Physical data (°C.) |
|---|---|---|---|---|---|---|---|---|
| 5.01 | $C_4H_9(t)$ | $CH_3$ | $CH_3$ | $Q_1$ | $CF_3$ | H | — | m.p. = 101–102° |
| 5.02 | $C_4H_9(t)$ | $CH_3$ | $CH_3$ | $Q_1$ | $CF_3$ | Br | — | m.p. = 53–55° |

-continued

| Compound | $R_1$ | $R_2$ | $R_3$ | $R_5$ | $R_6$ | $R_7$ | $R_8$ | Physical data (°C.) |
|---|---|---|---|---|---|---|---|---|
| 5.03 | $C_5H_{11}(t)$ | $CH_3$ | $CH_3$ | $Q_1$ | $CF_3$ | Br | — | oil* |
| 5.04 | $C_4H_9(t)$ | $CH_3$ | $CH_3$ | $Q_1$ | Cl | Cl | — | $n_D^{24} = 1.5868$ |
| 5.05 | $C_4H_9(t)$ | $CH_3$ | $CH_3$ | $Q_1$ | Cl | Br | — | $n_D^{23} = 1.5978$ |
| 5.06 | $C_4H_9(t)$ | $CH_3$ | $CH_3$ | $Q_1$ | Br | Br | — | $n_D^{24} = 1.6106$ |
| 5.07 | $C_4H_9(t)$ | $C_2H_5$ | $C_2H_5$ | $Q_1$ | $CF_3$ | Br | — | $n_D^{24} = 1.5476$ |
| 5.08 | $C_4H_9(t)$ | $CH_3$ | $CH_3$ | $Q_1$ | Br | Cl | — | $n_D^{24} = 1.5983$ |
| 5.09 | $C_4H_9(t)$ | $C_2H_5$ | $C_2H_5$ | $Q_1$ | Cl | Cl | — | $n_D^{24} = 1.5783$ |
| 5.10 | $C_4H_9(t)$ | $C_2H_5$ | $C_2H_5$ | $Q_1$ | Cl | Br | — | $n_D^{24} = 1.5892$ |
| 5.11 | $C_4H_9(t)$ | $CH_3$ | $CH_3$ | $Q_2$ | $CF_3$ | — | $CH_3$ | m.p. = 61–64° |
| 5.12 | $C_4H_9(t)$ | $CH_3$ | $CH_3$ | $Q_2$ | $CF_3$ | — | $C_3H_7(i)$ | m.p. = 81–82° |
| 5.13 | $C_4H_9(t)$ | $CH_3$ | $CH_3$ | $Q_2$ | $C_2F_5$ | — | $CH_3$ | m.p. = 55–57° |
| 5.14 | $C_4H_9(t)$ | $CH_3$ | $CH_3$ | $Q_2$ | $C_3F_7(n)$ | — | $CH_3$ | oil* |
| 5.15 | $C_4H_9(t)$ | $CH_3$ | $CH_3$ | $Q_3$ | $C_4H_9(t)$ | — | — | m.p. = 74–76° |
| 5.16 | $C_4H_9(t)$ | $C_2H_5$ | $C_2H_5$ | $Q_9$ | Cl | Cl | $CH_3$ | $n_D^{23} = 1.5615$ |
| 5.17 | $C_4H_9(t)$ | $CH_3$ | $CH_3$ | $Q_9$ | Cl | Cl | $CH_3$ | m.p. = 79.5–71.5° |
| 5.18 | cyclopentyl-H | $C_2H_5$ | $C_2H_5$ | $Q_1$ | Cl | Cl | — | $n_D^{23} = 1.5938$ |
| 5.19 | cyclopentyl-H | $C_2H_5$ | $C_2H_5$ | $Q_1$ | Cl | Br | — | $D_D^{22} = 1.6013$ |
| 5.20 | $C_4H_9(t)$ | $CH_3$ | $CH_3$ | $Q_5$ | $C_4H_9(t)$ | — | — | oil* |
| 5.21 | $C_4H_9(t)$ | $CH_3$ | $CH_3$ | $Q_2$ | $C_2F_5$ | — | $C_3H_7(i)$ | m.p. = 70–71° |
| 5.22 | $C_4H_9(t)$ | $CH_3$ | $CH_3$ | $Q_2$ | $C_3F_7(n)$ | — | $C_3H_7(i)$ | m.p. = 64–65° |
| 5.23 | $C_4H_9(t)$ | $C_2H_5$ | $C_2H_5$ | $Q_2$ | $CF_3$ | — | $C_3H_7(i)$ | m.p. = 50–51° |
| 5.24 | $C_4H_9(t)$ | $C_2H_5$ | $C_2H_5$ | $Q_2$ | $C_2F_5$ | — | $CH_3$ | oil* |
| 5.25 | $C_4H_9(t)$ | $C_2H_5$ | $C_2H_5$ | $Q_2$ | $C_2F_5$ | — | $C_3H_7(i)$ | m.p. = 46–47° |
| 5.26 | $C_4H_9(t)$ | $C_2H_5$ | $C_2H_5$ | $Q_2$ | $C_3F_7(n)$ | — | $CH_3$ | oil* |
| 5.27 | $C_4H_9(t)$ | $C_2H_5$ | $C_2H_5$ | $Q_2$ | $C_3F_7(n)$ | — | $C_3H_7(i)$ | m.p. = 39–41° |
| 5.28 | $C_4H_9(t)$ | $C_2H_5$ | $C_2H_5$ | $Q_2$ | $CF_3$ | — | $CH_3$ | m.p. = 43–44° |
| 5.29 | $C_4H_9(t)$ | $C_2H_5$ | $C_2H_5$ | $Q_3$ | $C_4H_9(t)$ | — | — | oil* |
| 5.30 | $C_4H_9(t)$ | $CH_3$ | $CH_3$ | $Q_3$ | $CF_3$ | — | — | $n_D^{20} = 1.5340$ |
| 5.31 | $C_3H_7(i)$ | $CH_3$ | $CH_3$ | $Q_3$ | $CF_3$ | — | — | $n_D^{20} = 1.5406$ |
| 5.32 | $C_4H_9(t)$ | $CH_3$ | $CH_3$ | $Q_4$ | $CH_3$ | — | — | $n_D^{25} = 1.5685$ |
| 5.33 | $C_3H_7(i)$ | $CH_3$ | $CH_3$ | $Q_4$ | $CH_3$ | — | — | $n_D^{40} = 1.5716$ |
| 5.34 | $C_4H_9(t)$ | $CH_3$ | $CH_3$ | $Q_9$ | Cl | Cl | $CH_3$ | m.p. = 70.5–71.5° |
| 5.35 | $C_4H_9(t)$ | $C_2H_5$ | $C_2H_5$ | $Q_9$ | Cl | Cl | $CH_3$ | $n_D^{23} = 1.5615$ |
| 5.36 | $C_4H_9(t)$ | $CH_3$ | $CH_3$ | $Q_1$ | Cl | $CH_3$ | — | $n_D^{26} = 1.5788$ |
| 5.37 | $C_4H_9(t)$ | $C_2H_5$ | $C_2H_5$ | $Q_1$ | Cl | $CH_3$ | — | $n_D^{26} = 1.5693$ |
| 5.38 | $C_4H_9(t)$ | $C_3H_7(i)$ | $C_3H_7(i)$ | $Q_1$ | Cl | Cl | — | $n_D^{27} = 1.5660$ |
| 5.39 | cyclopentyl-H | $C_3H_7(i)$ | $C_3H_7(i)$ | $Q_1$ | Cl | Cl | — | $n_D^{27} = 1.5798$ |
| 5.40 | $C_3H_7(i)$ | $CH_3$ | $CH_3$ | $Q_8$ | 6-Cl | 5-Cl | — | m.p. = 66–71° |
| 5.41 | $C_4H_9(t)$ | $CH_3$ | $CH_3$ | $Q_8$ | 6-Cl | 5-Cl | — | m.p. = 56–67° |

*structure accords with the proton resonance spectrum

The following carbodiimides of formula Ic' can also be prepared in accordance with the process described in Example 5:

| $R_1$ | $R_2$ | $R_3$ | $R_5$ | $R_6$ | $R_7$ | $R_8$ |
|---|---|---|---|---|---|---|
| $C_4H_9(t)$ | $C_3H_7(i)$ | $C_3H_7(i)$ | $Q_1$ | Cl | $CH_3$ | — |
| $C_5H_{11}(t)$ | $C_2H_5$ | $C_2H_5$ | $Q_1$ | Cl | Cl | — |
| $C_4H_9(s)$ | $C_2H_5$ | $C_2H_5$ | $Q_1$ | Cl | Cl | — |
| $C_3H_7(i)$ | $C_2H_5$ | $C_2H_5$ | $Q_1$ | Cl | Cl | — |
| cyclopentyl-H | $CH_3$ | $CH_3$ | $Q_1$ | Cl | $CH_3$ | — |
| cyclopentyl-H | $C_2H_5$ | $C_2H_5$ | $Q_1$ | Cl | $CH_3$ | — |
| $C_5H_{11}(t)$ | $CH_3$ | $CH_3$ | $Q_1$ | Cl | $CH_3$ | — |
| $C_5H_{11}(t)$ | $C_2H_5$ | $C_2H_5$ | $Q_1$ | Cl | $CH_3$ | — |
| $C_5H_{11}(t)$ | $C_3H_7(i)$ | $C_3H_7(i)$ | $Q_1$ | Cl | $CH_3$ | — |
| $C_3H_7(i)$ | $C_2H_5$ | $C_2H_5$ | $Q_1$ | Cl | $CH_3$ | — |
| $C_4H_9(t)$ | $CH_3$ | $CH_3$ | $Q_1$ | Br | $CH_3$ | — |
| $C_4H_9(t)$ | $C_2H_5$ | $C_2H_5$ | $Q_1$ | Br | $CH_3$ | — |
| $C_4H_9(t)$ | $C_3H_7(i)$ | $C_3H_7(i)$ | $Q_1$ | Br | $CH_3$ | — |
| $C_4H_9(t)$ | $CH_3$ | $CH_3$ | $Q_1$ | $CH_3$ | $CH_3$ | — |
| $C_4H_9(t)$ | $C_2H_5$ | $C_2H_5$ | $Q_1$ | $CH_3$ | $CH_3$ | — |
| $C_4H_9(t)$ | $CH_3$ | $CH_3$ | $Q_4$ | $C_2H_5$ | — | — |
| $C_4H_9(t)$ | $C_2H_5$ | $C_2H_5$ | $Q_4$ | $C_2H_5$ | — | — |

-continued

| R₁ | R₂ | R₃ | R₅ | R₆ | R₇ | R₈ |
|---|---|---|---|---|---|---|
| $C_4H_9(t)$ | $CH_3$ | $CH_3$ | $Q_4$ | $C_3H_7(i)$ | — | — |
| $C_4H_9(t)$ | $C_2H_5$ | $C_2H_5$ | $Q_4$ | $C_3H_7(i)$ | — | — |
| ⬠H | $CH_3$ | $CH_3$ | $Q_1$ | $CF_3$ | H | — |
| ⬠H | $CH_3$ | $CH_3$ | $Q_1$ | $CF_3$ | Br | — |
| ⬠H | $CH_3$ | $CH_3$ | $Q_1$ | $CF_3$ | H | — |
| $C_4H_9(t)$ | $CH_3$ | $CH_3$ | $Q_1$ | Br | H | — |
| $C_5H_{11}(t)$ | $CH_3$ | $CH_3$ | $Q_1$ | Br | H | — |

The following carbodiimides of formula Ic are also prepared as described in Example 5:

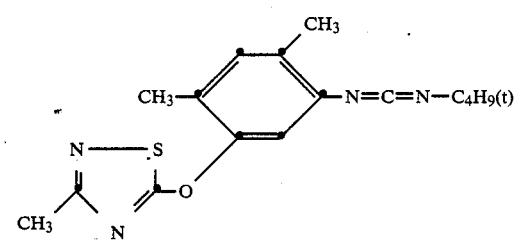

$n_D^{25} = 1.5632$
(compound 5.42)

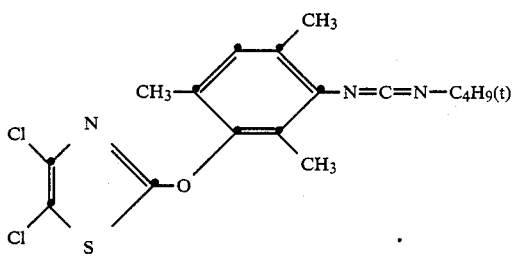

pale oil
(compound 5.43)

EXAMPLE 6

Action against Tetranychus urticae (OP-sensitive) and Tetranychus cinnabarinus (OP-tolerant)

12 hours before the test for acaricidal action, the primary leaves of Phaseolus vulgaris plants are infected with an infested piece of leaf from a mass culture of Tetranychus urticae (OP-sensitive) or Tetranychus cinnabarinus (OP-tolerant). (The tolerance refers to the tolerance to diazinone). The treated infested plants are sprayed to drip point with an emulsified test solution containing the respective test compound in a concentration of 400 ppm. A count of the number of living and dead imagines and larvae (all mobile stages) is made under a stereoscopic microscope after 24 hours and again after 6 days (T. urticae) and after 7 days (T. cinnabarinus). One plant is used for each test species. During the test run, the plants are kept in greenhouse compartments at 25° C. and c. 50–60% relative humidity.

In this test, compounds of formula I according to Examples 3, 4 and 5 exhibit good activity against Tetranychus urticae and Tetranychus cinnabarinus.

EXAMPLE 7

Ovicidal action against Tetranychus urticae (OP-resistant)

Potted phaseolus vulgaris plants in the primary leaf stage are each populated twice with 30 females of Tetranychus urticae. After oviposition for 24 hours, the females are removed from the plants with a suction pump (water jet pump), so that only the egg deposits on the plants remain. The egg-infested plants are then sprayed to drip point with an aqueous emulsion containing 400 ppm of the test compound and kept for 5 days at 25° C. and about 50% relative humidity. After this time a count is made to determine the percentage mortality of the eggs and of hatched out larvae.

Compounds of formula I according to Example 3, 4 and 5 exhibit good activity in this test.

EXAMPLE 8

Miticidal leaf penetration action against Tetranychus cinnabarinus

Potted dwarf bean plants in the primary leaf stage infested with Tetranychus cinnabarinus are used for the test. The plants are populated with the mites one day before the application of the test compound.

The surface of the leaves of the plants infected with the mites are sprayed with an emulsion formulation containing 400 ppm of the test compound. After the spray coating has dried, a ribbon of viscous glue (caterpillar glue) is applied to the edge of the surface of each of a number of infested leaves so as to prevent the mites from migrating from the underside to the surface of the leaf.

The treated plants are then kept in a greenhouse at a temperature of 25°–27° C. and a relative humidity of c. 50%. Six days after application the plants are examined to ascertain whether a tranlaminar effect has occured, i.e. penetration of the test compound from the surface to the underside of the leaf, by determining the percentage mortality of the eggs and larval as well as adult stages.

Compounds of formula I according to Examples 3, 4 and 5 exhibit good activity in this test.

EXAMPLE 9

Action against Panonychus ulmi (OP and carbamate resistant)

Potted apple seedlings with about 20 to 30 leaves are each populated with 60 adult females of Panonychus ulmi. The infested plants are sprayed after 7 days to drippoint with an aqueous emulsion containing 400 ppm of the test compound. The treated plants are then stood in a greenhouse for a further 14 days at 25° C. and about 50% relative humidity.

After this time, evaluation is made by taking 20 leaves from each plant, removing the mite population from these leaves by means of a brushing device and counting the number of eggs, postembryonic stages and adults under a stereoscopic microscope. An assessment is made of the percentage reduction of the mite population as compared with untreated controls.

Compounds of formula I according to Example 3, 4 and 5 exhibit good activity in this test.

EXAMPLE 10

Action against parasitic mites in animals

Batches consisting of about 50 mites in different stages (larvae, nymphs and imagines) are taken from hens infested with Dermanyssae gallinae. The batches are each treated with an aqueous emulsion, suspension or solution containing 800 ppm of the test compound by pouring the liquid formulation of the test compound on to the mites present in a test tube. The liquid formulation is then absorbed by a cotton wool plug. The treated mites remain in the test tube for 72 hours, after which time the percentage mortality of the treated mites is determined in comparison with untreated controls.

Compounds of formula I according to Examples 3, 4 and 5 exhibit good activity in this test.

EXAMPLE 11

Action against ticks: killing action in various development stages

About 50 larvae, about 25 nymphs or about 10 imagines of each of the tick species Phipicephalus bursa, Amblyomma hebraeum and Boophilus microplus are used as test organisms. The test organisms are immersed for a short time in aqueous emulsions containing the respective test compound in a concentration of 400 ppm. The emulsions, which are contained in test tubes, are then absorbed by cotton wool, and the wetted test organisms are left in the test tubes which have thus been contaminated. Evaluation of the percentage mortality is made 3 days later in the case of the larvae and 14 days later in the case of the nymphs and imagines.

Compounds of formula I according to Examples 3, 4 and 5 are very effective in this test.

EXAMPLE 12

Action against ticks: inhibition of oviposition

Adult females of the cattle tick Boophilus microplus which are fully replete with blood are used as test organisms. 10 ticks of an OP-sensitive strain (e.g. Biarra strain) and 10 ticks of a normally sensitive strain (e.g. Yeerongpilly strain) are treated. The ticks are affixed to plates to which double-sided adhesive tape has been applied and are then either wetted with aqueous emulsions or solutions containing 800 ppm of the test compound or are brought into contact with cotton wool which has been impregnated with these liquids. The ticks are subsequently kept in a climatic chamber under constant conditions. Evaluation is made after 3 weeks. The percentage inhibition of the deposit of fertile eggs is determined in comparison with untreated controls.

Compounds of formula I according to Examples 3, 4 and 5 exhibit good activity in this test.

EXAMPLE 13

Action against Musca domestica 50 g of freshly prepared nutrient substrate for maggots are charged into each of a number of beakers. A specific amount of an acetonic solution containing 1% by weight of the respective test compound is pipetted onto the nutrient substrate present in the beakers to give an active ingredient concentration of 800 ppm. The substrate is then thoroughly mixed and the acetone subsequently allowed to evaporate over a period of at least 20 hours.

Then 25 one-day-old maggots of Musca domestica are put into each of the beakers containing the treated nutrient substrate for testing with each active ingredient. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formula I according to Examples 3, 4 and 5 exhibit good activity in this test.

EXAMPLE 14

Insecticidal action against feeding insects

Cotton plants about 20 cm high, in pots, are sprayed with aqueous emulsions (obtained from a 10% emulsifiable concentrate) which contain the respective test compound in a concentration of 400 ppm. After the spray coating has dried, the cotton plants are populated with Spodoptera littoralis and Heliothis virescens larvae in the $L_3$-stage. The test is carried out at 24° C. and 60% relative humidity. Mortality as well as inhibition of development and moulting of the test insects are determined at intervals of 48 and 96 hours respectively.

Compounds of formula I according to Examples 3, 4 and 5 exhibit good activity in this test.

EXAMPLE 15

Action against Lucilia sericata 1 ml of an aqueous solution containing 0.5% of test compound is added to 9 ml of a culture medium. Then about 30 freshly hatched Lucilia sericate larvae are added to the culture medium, and the insecticidal action is determined after 48 and 96 hours by evaluating the mortality rate.

The compounds of formula I according to Examples 3, 4 and 5 exhibit good activity against in this test.

EXAMPLE 16

Action against Aëdes aegypti

A concentration of 400 ppm is obtained by pipetting a specific amount of a 0.1% solution of the test compound in acetone on to the surface of 150 ml of water in a beaker. After the acetone has evaporated, 30 to 40 two-day-old larvae of Aëdes aegypti are put into the beaker containing the test compound. Mortality counts are made after 2 and 7 days.

The compounds of formula I according to Examples 3, 4 and 5 exhibit good activity in this test.

EXAMPLE 17

Formulations for active ingredients of formula I or combinations thereof with other insecticides or acaricides (throughout, percentages are by weight)

| 1. Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether | — | 2% | — |

| 1. Wettable powders | (a) | (b) | (c) |
|---|---|---|---|
| (7–8 moles of ethylene oxide) | | | |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| compound of formula I or combination | 10% |
| octylphenol polyethylene glycol ether (4–5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carrier, and grinding the mixture in a suitable mill.

| 4. Extruder granulate | |
|---|---|
| compound of formula I or combination | 10% |
| sodium lignosulfonate | 2% |
| carboxymethylcellulose | 1% |
| koalin | 87% |

The active ingredient or combination is mixed and ground with the adjuvants, and the mixture is subsequently moistened with water. The mixture is extruded and then dried in a stream of air.

| 5. Coated granulate | |
|---|---|
| compound of formula I or combination | 3% |
| polyethylene glycol 200 | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |

| 6. Suspension concentrate | |
|---|---|
| water | 32% |

The finely ground active ingredient or combination is intimately mixed with the adjuvants, giving a suspension concentrate from which suspensions of any desired concentration can be obtained by dilution with water.

What is claimed is:

1. A compound of formula I $$\text{(I)}$$

(structure: benzene ring with substituents $R_5$–O, $R_2$, Z–$R_1$, $R_3$, $R_4$)

wherein

Z is $$-NH-\overset{S}{\underset{\parallel}{C}}-NH-; \quad -N=C\overset{S-R_9}{\underset{NH-}{\diagdown}}$$

or $-N=C=N-$;

$R_1$ is $C_1$–$C_{12}$alkyl, $C_3$–$C_{10}$alkenyl, $C_3$–$C_{10}$alkynyl, $C_3$–$C_8$cycloalkyl, $C_1$–$C_3$alkyl substituted by 1 or 2 $C_3$–$C_6$cycloalkyl radicals, or is alkoxyalkyl containing a total of 3 to 10 carbon atoms, halogen-substituted $C_1$–$C_{12}$alkyl, polycyclic $C_7$–$C_{10}$cycloalkyl, or phenyl($C_1$–$C_5$)alkyl which may be substituted in the phenyl moiety by 1 or 2 identical or different members selected from the group consisting of halogen, methoxy, ethoxy and $C_1$–$C_5$alkyl, $R_2$ is hydrogen or $C_1$–$C_5$alkyl, $R_3$ is $C_1$–$C_5$alkyl or $C_3$–$C_6$cycloalkyl, $R_4$ is hydrogen or $C_1$–$C_4$alkyl, $R_5$ is a thiazole or benzthiazole radical which radical may be substituted at the carbon or nitrogen atoms by 1 to 3 of the substituents $R_6$, $R_7$ and $R_8$, $R_6$ and $R_7$ are each independently of the other hydrogen, halogen, $C_1$–$C_4$alkyl, halogen-substituted $C_1$–$C_4$alkyl, $C_1$–$C_4$alkoxy, halogen-substituted $C_1$–$C_4$alkoxy, phenyl, or $C_1$–$C_4$-alkylthio, $R_8$ is hydrogen or $C_1$–$C_4$alkyl, and $R_9$ is $C_1$–$C_5$alkyl, $C_2$–$C_5$alkenyl, $C_3$–$C_4$alkynyl, alkoxyalkyl containing a total of 10 carbon atoms, or alkylthioalkyl containing a total of 10 carbon atoms or a salt thereof with an acid or a base.

2. A compound of formula I according to claim 1, wherein $R_5$ is a heterocyclic radical selected from the group consisting of (thiazole structure with $R_6$, $R_7$) and (benzthiazole structure with $R_6$, $R_7$)

3. A compound of formula I according to either claim 1 or claim 2, wherein the group $R_5O$ is para-position to the group Z, $R_1$ is $C_3$-$C_7$alkyl, cyclopentyl, cyclohexyl, (dicyclopropyl)methyl, or alkoxyalkyl of 4 carbon atoms, $R_2$ and $R_3$ are each independently of the other $C_1$-$C_3$alkyl, $R_4$ is hydrogen, $R_6$ is hydrogen, chlorine, bromine, $C_1$-$C_4$alkyl, $C_1$-$C_3$perfluoralkyl, or phenyl;

$R_7$ is hydrogen, chlorine, bromine, or $C_1$-$C_4$alkyl, $R_8$ is hydrogen, or $C_1$-$C_3$alkyl, and $R_9$ is methyl or ethyl, or a salt thereof with a hydrohalic acid.

4. A compound of formula I according to claim 1, wherein the group $R_5O$ is in para-position to the group Z, $R_1$ is tert-butyl, tert-pentyl, $C_5$-$C_6$cycloalkyl or 3-methoxypropyl, $R_2$ and $R_3$ are each independently of the other $C_1$-$C_3$alkyl, $R_4$ is hydrogen, $R_5$ is

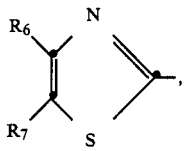

$R_6$ is $C_1$-$C_4$alkyl, chlorine, bromine, or $C_1$-$C_3$perfluoroalkyl, $R_7$ is hydrogen, chlorine, bromine or $C_1$-$C_4$alkyl, $R_8$ is $C_1$-$C_3$alkyl, and $R_9$ is methyl or ethyl, or a salt thereof with a hydrohalic acid.

5. A thiourea of formula Ia

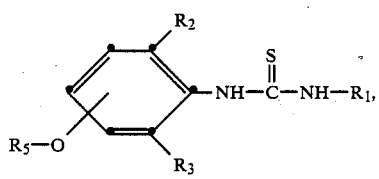

according to claim 1, wherein $R_1$ is tert-butyl, isopropyl, cyclopentyl, cyclohexyl, (dicyclopropyl)methyl, 2,4-dimethylpentan-3-yl or tert-pentyl, $R_2$ and $R_3$ are each independently of the other methyl, ethyl or isopropyl $R_5$ is

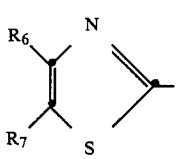

$R_6$ is chlorine, bromine $CF_3$, $C_2F_5$, methyl or tert-butyl, $R_7$ is hydrogen, bromine, chlorine or methyl and $R_8$ is mehtyl or isopropyl.

6. An isothiourea of formula Ib

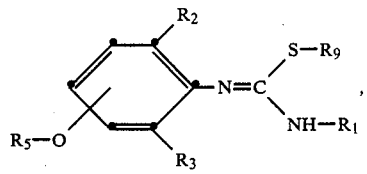

according to claim 1, wherein $R_1$ is tert-butyl, isopropyl, cyclopentyl, cyclohexyl, tert-pentyl, 2,4-dimethylpentan-3-yl or (dicyclopropyl)methyl, $R_2$ and $R_3$ are each independently of the other methyl or ethyl or isopropyl, $R_5$ is

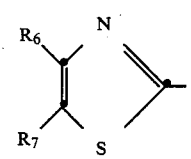

$R_6$ is chlorine, bromine, methyl, pentafluoroethyl or trifluoromethyl, $R_7$ is hydrogen, bromine, chlorine, or methyl, $R_8$ is methyl or isopropyl, and $R_9$ is methyl or ethyl, or a salt thereof with a hydrohalic acid.

7. A carbodiimide of formula Ic

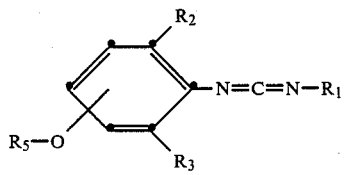

according to claim 1, wherein $R_1$ is tert-butyl, cyclopentyl or tert-pentyl, $R_2$ and $R_3$ are each independently of the other methyl, ethyl or isopropyl, $R_5$ is

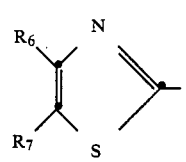

$R_6$ is chlorine, bromine, methyl, tert-butyl, pentafluoroethyl or trifluoromethyl;

$R_7$ is chlorine, bromine, or methyl, and $R_8$ is methyl or isopropyl.

8. A compound of formula Ia, Ib or Ic according to any one of claims 5, 6 or 7, wherein the group $R_5$—O— is in para-position.

9. A compound according to claim 6 of formula

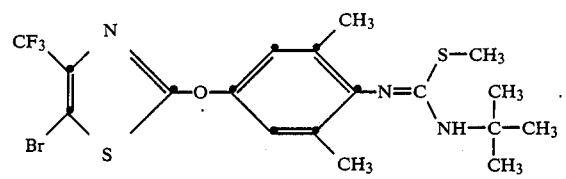

10. A compound according to claim 6 of formula

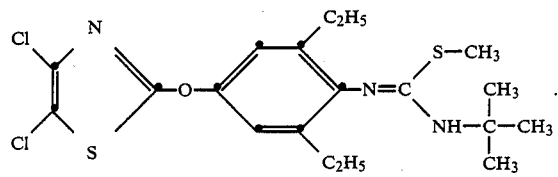

11. A compound according to claim 7 of formula

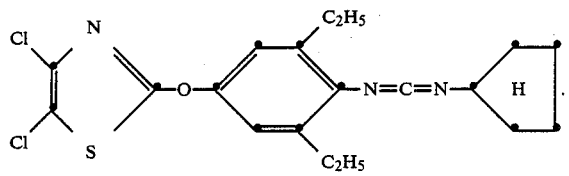

12. A compound according to claim 7 of formula

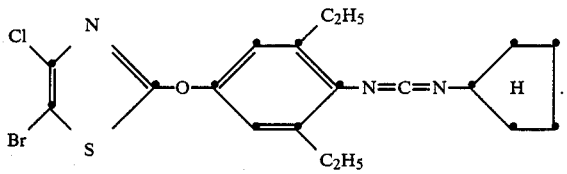

13. A compound according to claim 5 of formula

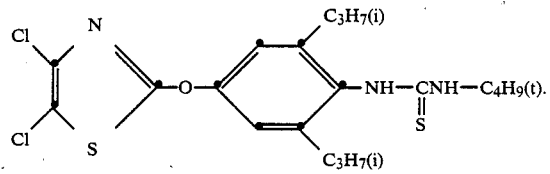

14. A compound according to claim 6 of formula

15. A compound according to claim 7 of formula

16. A compound according to claim 6 of formula

17. An insecticidal and acaricidal composition which contains, as active component, a compound as claimed in claim 1 together with an inert carrier.

18. A method of controlling insects and representatives of the order Acarina, which comprises treating or contacting said pests, their various development stages or the locus thereof, with a pesticidally effective amount of a compund of formula I according to claim 1 or with a composition which contains a pesticidally effective amount of such a compound, together with adjuvants and carriers suitable therefor.

19. Method according to claim 18 for controlling insects and representatives of the order Acarina that are pests of animals and plants.

20. Method according to claim 19 for controlling ticks and mites.

21. Method according to claim 20 for controlling plant-destructive mites.

22. Method according to claim 19 for controlling plant-destructive insects.

* * * * *